(12) United States Patent
Olson et al.

(10) Patent No.: US 8,818,523 B2
(45) Date of Patent: Aug. 26, 2014

(54) RECHARGE OF AN IMPLANTABLE DEVICE IN THE PRESENCE OF OTHER CONDUCTIVE OBJECTS

(75) Inventors: David P. Olson, Minnetrista, MN (US); Todd A. Kallmyer, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 52 days.

(21) Appl. No.: 13/455,690

(22) Filed: Apr. 25, 2012

(65) Prior Publication Data

US 2013/0289662 A1  Oct. 31, 2013

(51) Int. Cl.
*A61N 1/00* (2006.01)
*A61N 1/378* (2006.01)
*H02J 7/02* (2006.01)

(52) U.S. Cl.
CPC ............... *A61N 1/3787* (2013.01); *H02J 7/025* (2013.01)
USPC ............................................. 607/61; 320/108

(58) Field of Classification Search
CPC .......... A61N 1/3787; A61N 1/08; H02J 7/025
USPC ................................. 607/33, 60–61; 320/108
See application file for complete search history.

(56) References Cited

U.S. PATENT DOCUMENTS

| | | | |
|---|---|---|---|
| 6,327,504 B1 * | 12/2001 | Dolgin et al. | 607/61 |
| 7,211,986 B1 | 5/2007 | Flowerdew et al. | |
| 7,248,017 B2 | 7/2007 | Cheng et al. | |
| 7,521,890 B2 | 4/2009 | Lee et al. | |
| 2005/0075697 A1 * | 4/2005 | Olson et al. | 607/61 |
| 2006/0190048 A1 | 8/2006 | Gerber | |
| 2008/0303480 A1 | 12/2008 | Prutchi et al. | |
| 2009/0079268 A1 | 3/2009 | Cook et al. | |
| 2009/0134713 A1 | 5/2009 | Stevens et al. | |
| 2009/0206791 A1 | 8/2009 | Jung | |
| 2010/0219351 A1 * | 9/2010 | Roberts et al. | 250/393 |
| 2010/0268305 A1 * | 10/2010 | Olson et al. | 607/61 |
| 2011/0298420 A1 * | 12/2011 | Forsberg et al. | 320/108 |
| 2011/0301669 A1 * | 12/2011 | Olson et al. | 607/61 |
| 2012/0262108 A1 * | 10/2012 | Olson et al. | 320/108 |

* cited by examiner

*Primary Examiner* — Catherine Voorhees
(74) *Attorney, Agent, or Firm* — Beth L. McMahon

(57) ABSTRACT

Techniques are disclosed for controlling the transcutaneously transfer of energy to an implantable medical device (IMD) that is in proximity to a conductive object that conducts current in the presence of an electromagnetic field. Various techniques are disclosed for estimating or determining the levels of heat dissipation associated with the object during the transfer of energy. If too much heat is being dissipated, the transfer of energy may be adjusted so that heating remains below acceptable levels.

28 Claims, 11 Drawing Sheets

RECHARGE OF AN IMPLANTABLE DEVICE IN THE PRESENCE OF OTHER CONDUCTIVE OBJECTS

BACKGROUND

Implantable medical devices for producing a therapeutic result in a patient are well known. Examples of such implantable medical devices include implantable drug infusion pumps, neurostimulators, cardioverters, cardiac pacemakers, defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform sensing and/or therapeutic functions. Sensing functions may involve the sensing, storing and/or reporting of physiological parameters. Therapeutic functions may include driving an electrical infusion pump, providing an electrical neuro stimulation pulse or providing an electrical cardiac stimulation pulse.

Some implantable medical devices can receive electrical power transcutaneously through the use of inductive coupling. For instance, power can be transferred by inductively coupling an external primary coil that is positioned on or near the skin of a patient with a secondary coil that is coupled to, or included within, an implantable medical device. Current induced in the secondary coil may be used to store energy in a power source such as a rechargeable battery and/or could be used to directly power circuitry within the implantable device. Once recharged, the internal power source may be used to supply electrical power to the implanted medical device.

Many devices and techniques have been developed to provide transcutaneous energy to power an implantable medical device and/or to recharge a power source associated with the device. As previously noted, techniques generally employ a primary coil driven by an external power source.

SUMMARY

Techniques are disclosed for transcutaneously transferring energy to an implantable medical device (IMD). The IMD may be adapted to deliver a type of therapy to the patient, which may include electrical stimulation and/or drug therapy. Alternatively, the IMD may be adapted to sense one or more signals from a patient. Many types of implantable medical devices may utilize the disclosed systems and techniques, including implantable therapeutic substance delivery devices, drug pumps, cardiac pacemakers, cardioverters or defibrillators, and/or devices to deliver electrical stimulation pulses for a neurological or muscular condition. Other specific examples include devices to provide therapy to treat chronic pain, tremor, Parkinson's disease, epilepsy, urinary or fecal incontinence, sexual dysfunction, obesity, or gastroparesis. Such therapy may be delivered via one or more therapy connections, which may be one or more leads and/or catheters.

As described herein, transfer of energy to an IMD may be performed to recharge a rechargeable power source of the IMD such as a battery or capacitor. Such transfer of energy may additionally or alternatively be performed to allow the IMD to operate directly from the provided energy before that energy is stored within a power source.

According to the current disclosure, the transfer of energy may be performed in the presence of a conductive object. As used herein, a conductive object is a collection of one or more objects that are positioned in, or on, one or more locations of the patient's body and which may be electrically conductive in the presence of an electromagnetic field. For instance, such conductive objects may be formed in whole or in part of a material that is metallic, a semi-conductor, magnetic, or any other material that will conduct a current in the presence of an electromagnetic field. A conductive object may comprise one or more bone screws or plates, artificial body parts such as artificial hips, shoulders, and the like, surgical staples or other objects. A conductive object may further comprise a therapy delivery device such as lead, a leadless electrode, an electrical stimulation or drug therapy device, and/or a power source of such a therapy device that is housed outside of (e.g., umbilically connected) the device, and so on.

A conductive object may, but need not be, implanted. For instance, metallic medical devices may be worn or otherwise carried on the exterior of the patient's body. Still other objects worn on the patient's body may include medical monitors, external stimulation devices and/or pumps, and so on. Non-medical objects such as jewelry, belt buckles, metal electronics carried in pockets, and so on, may likewise be carried by the patient. Any such one or more objects that will conduct current when placed within an electromagnetic field may affect recharge and are ideally taken into account when transferring energy to an IMD (e.g., to recharge a rechargeable power source.).

Various techniques are described herein for estimating or determining an amount of power being dissipated by a conductive object in proximity to an IMD. As used herein, "proximity" refers to being in a location such that the electromagnetic field used to transfer energy to the IMD is also inducing a current within the other conductive object so that heat may be associated with this other object during the transfer of energy to the IMD.

According to one example technique, power may be delivered from a primary coil of an external charging device to an IMD in the known absence of a conductive object. The amount of power being delivered by the primary coil may be determined based on the total power at which the primary coil is being driven less any heat being dissipated by the primary coil, a value which may be determined based on a known AC series resistance of the primary coil. While this power level is being delivered by the primary coil, the recharge power delivered to a rechargeable power source of the IMD may be measured. This may be accomplished by determining the recharge current and voltage levels associated with the rechargeable power source, both of which may be measured and communicated telemetrically to the external device, if desired. In some cases wherein recharge voltage is substantially constant throughout most of a recharge session, it may be sufficient to merely determine a recharge current level during recharge.

Later, when a conductive object is known to be in proximity to the IMD while energy is being transferred to the IMD, the primary coil may be driven with a power level that achieves substantially a same recharge power level (or, in some examples, a same recharge current while assuming recharge voltage is constant) as was obtained the conductive object was known to be absent. The power level that is transmitted by the primary coil to achieve this same power level (or current level) to the rechargeable power source of the IMD may be determined. Any increase in the power level transmitted by the primary coil to achieve the same recharge conditions in the IMD may be estimated as being the power absorbed by the conductive object. Transfer of energy from the primary coil may then be controlled based on any such increase of the transferred power level that is necessary to achieve the same recharge conditions in the IMD when the conductive object is present as compared to when the object is absent. Control over the transfer of energy may be accomplished by modulating a signal associated with driving the primary coil, such as a voltage or duty cycle associated with generating an energy transfer signal in the primary coil.

In another example, an amount of power being absorbed by the conductive object may be determined by determining total power transmitted by the primary coil, the amount of power that is being supplied to the power source of the IMD and the amount of power that is being dissipated as heat by the IMD. The amount of power supplied to the rechargeable power source and the heat dissipated by the IMD may be subtracted from the total amount of power transmitted by the primary coil. It may be determined that the remainder is being absorbed by the conductive object. If the amount of power absorbed by the conductive object exceeds some acceptable threshold limit, it may be desirable to control energy transfer from the primary coil to the IMD based on the amount by which the threshold is exceeded.

As yet another example, a corresponding loading profile may be determined for the system when energy is being transferred by the primary coil in the presence of the conductive object. Another loading profile may be determined when energy is being transferred by the primary coil in the absence of the conductive object. A loading profile measures power delivered by the primary coil as a frequency of the recharge signal is varied. At the resonant frequency, a peak-to-baseline ratio of power levels may be determined. This is the ratio between the peak power level transferred by the primary coil at resonant frequency and the baseline power level, which is the power level that would be transferred at that frequency if that frequency were not a resonant frequency of the system. The baseline power level may be determined, for instance, by extrapolating portions of a loading profile curve that are not associated with resonant frequency. A peak-to-baseline ratio may, in some examples, be smaller in the presence of a conductive object than would be the case in the absence of this object. The amount of change in this ratio may be used to estimate heating of the conductive object, and in turn, to determine whether, and by how much, an amount of power being transferred by the primary coil must be limited.

Other aspects of the loading profiles may be used to determine if, and how, to control energy transfer to the IMD. For instance, in some cases, the presence of a conductive object may change a resonant frequency of the system. The amount by which the resonant frequency is changed may be used to control energy transfer.

In other examples, comparing the loading profiles obtained both in the presence and absence of a conductive object may reveal frequency ranges over which recharge may be effectively conducted to transfer an acceptable amount of energy to the IMD power source while still limiting heating of the IMD. Although such frequency ranges may not exactly coincide with a resonant frequency of the system, the ranges may provide a frequency at which an acceptable level of energy transfer may never-the-less occur with minimal heating of the conductive object.

Still other examples control energy transfer based on a change in the effective AC series resistance of the primary coil at resonant frequency. In particular, the effective AC series resistance of the coil in the presence of the conductive object is compared to the effective resistance in the absence of the conductive object. An increase in the resistance of the coil as seen by the charging circuit indicates additional loading by the conductive object, and can be used to determine if, and how, energy transfer is controlled.

In still another embodiment, positional maps may be developed that correlate an amount of heating of the conductive object to a relative position and orientation existing between a primary and secondary coil. According to such techniques, triangulating antennas, antennas to determine signal strength indication (SSI) values and/or other sensors such as accelerometers may be used to determine a relative positioning between primary and second coils. Power data (e.g., power transmitted by primary coil, power provided to rechargeable power source of IMD, etc.) may be determined and associated with each relative position between the primary and secondary coils both in the presence and absence of a conductive object. This data may then be used to select a relative position between primary and secondary coils that will provide an adequate recharge current to a power source of the IMD while maintaining heating of the conductive object below corresponding thresholds. In one example, one or more such acceptable positions between the primary and second coils may be determined using the positional maps. A user interface may then provide visual and/or audio feedback to guide a user in positioning the primary coil into one of these saved locations so that a successful recharge session may be conducted. For instance, the system may use visual or audio feedback to help a user position the primary coil in a location that will result in adequate recharge current but will not result in exceeding any heat threshold limits.

According to the foregoing, in one embodiment, a system comprises a primary coil configured to transcutanously transfer energy to an implantable medical device (IMD) that is located in proximity to a conductive object. A circuit is configured to control the transfer of energy based on an estimated amount of heat associated with the object during the transfer of energy. For instance, the estimated amount of heat may be determined based on a difference between an amount of power delivered by a primary coil of an external recharging device in the presence of the conductive object to achieve a predetermined level of power delivered to a rechargeable power source of the IMD as compared to an amount of power delivered by the primary coil in the absence of the conductive object to achieve the same predetermined level of power delivered to the rechargeable power source. Any additional power provided by the primary coil in the presence of the object may be assumed to be dissipated by the object as heat. Control over the energy transfer may then be based on this estimated amount of heat.

In another example, the circuit of the foregoing paragraph may be configured to determine the amount of heat dissipated by the object and to control the transfer of energy based on the determined amount. The amount of heat dissipated may be determined, for instance, by determining an amount of power provided to a rechargeable power source of the IMD and an amount of heat determined to be dissipated by the IMD, both of which may be subtracted from the total amount of power delivered by the primary coil. The remainder of power may be assumed to be delivered to the conductive object.

In some scenarios, the circuit discussed above may be configured to vary a frequency at which the primary coil is driven to determine respective loading profiles of the system in the presence of the object and in the absence of the object, and to control the transfer of energy based on the respective loading profiles. The circuit may further be configured to control the transfer of energy based on a peak-to-baseline ratio indicated by at least one of the respective loading profiles.

In some examples, the circuit may be configured to control the transfer of energy based on at least one predetermined characteristic of the object. Such predetermined characteristics may include size, shape, and material used to construct the object. For instance, a relatively large component such as an artificial hip may be capable of absorbing more heat due to power losses than a small bone screw. Moreover, some materials will increase in temperature faster than other materials. Additionally, the location within the patient's body of the conductive may affect the power losses that may be tolerated. The relative location of the IMD and the conductive object may likewise affect the amount of power losses that will be considered acceptable. Such factors may be used to determine a maximum amount of power lost to heat that can be associated with a given conductive object.

The circuit may further be configured to control the transfer of energy based on heating of the IMD. That is, not only is heating associated with the conductive object used to control the transfer of energy, but a determined amount of heat dissipated by IMD may also be used to control the energy transfer. For instance, if the heating of the IMD is determined to be above a threshold amount, the power delivered by the primary coil may be reduced to maintain safe and comfortable recharge conditions.

In still other cases, the circuit may be configured to control the transfer of energy based on a change in a ratio of power delivered to a power source of the IMD and total heat dissipation within the system.

In some examples, one or more positional maps may be used to control energy transfer. For instance, the circuit may be configured to control the transfer of energy based on a positional map containing associations, each association associating a relative position between the primary coil and a secondary coil of the IMD and an indication of a power level obtained when energy is transferred from the primary coil to the secondary coil when the primary coil is in the relative position with respect to the secondary coil. One or more of the relative positions between the primary coil and the secondary coil may be selected based on this positional map for use in transferring energy from the primary coil to the secondary coil. Feedback may be provided to a user to guide the user in locating the primary coil in one of the relative positions with respect to the secondary coil.

The system may also comprise the IMD, which may be configured to perform at least one of providing a therapy and sensing a signal.

Another aspect of the disclosure may include a method, comprising transcutanously transferring energy to an implantable medical device (IMD) that is located in proximity to a conductive object and controlling the transcutaneous transfer of energy based on an estimated amount of heat associated with the object during the transfer of the energy. The method may further comprise determining the amount of heat dissipated by the object and wherein controlling the transfer of energy comprises controlling the transfer of energy based on the determined amount of heat dissipated by the object. As previously discussed, such determined amount of heat may be determined based on an amount of power determined to be delivered to a power source of an IMD and an amount of heat dissipated by the IMD.

The method may further comprise varying a frequency at which the transfer of energy occurs to determine a loading profile and wherein controlling the transfer of energy comprises controlling the transfer of energy based on the loading profile. A difference between a resonant frequency of the determined loading profile and a resonant frequency of a reference loading profile may be determined, for instance. Controlling the transfer of energy may comprise controlling the transfer of energy based on the difference. Alternatively or additionally, a peak-to-baseline ratio for power delivery at a resonant frequency of a system may be determined. The transfer of energy may comprise controlling the transfer of energy based on the peak-to-baseline ratio.

In some cases, the transfer of energy may be controlled based on at least one predetermined characteristic of the object. Alternatively or additionally, control over the transfer of energy may be based on at least one of heat dissipated by the primary coil and heat dissipated by the IMD.

Another example provides a system, comprising means for transcutanously transferring energy to an implantable medical device (IMD) that is located in proximity to a conductive object and means for controlling the transfer of energy to the IMD based on an estimated amount of heat associated with the object during the transfer of energy.

Still other aspects relate to a non-transitory storage medium for storing instructions to cause a control circuit to perform a method comprising transcutanously transferring energy to an implantable medical device (IMD) that is located in proximity to a conductive object and controlling the transfer of energy based on an estimated amount of heat associated with the object during the transfer of energy. The estimated amount of heat associated with the object may be estimated based on a difference between an amount of power delivered by a primary coil in the presence of the conductive object to achieve a predetermined level of power delivered to a rechargeable power source of the IMD as compared to an amount of power delivered by the primary coil in the absence of the conductive object to achieve the predetermined level of power delivered to the rechargeable power source.

The method may further comprise varying a frequency at which the transfer of energy occurs to determine a loading profile and wherein controlling the transfer of energy comprises controlling the transfer of energy based on a characteristic of the loading profile. Alternatively or additionally, the method may further comprise determining respective loading profiles in the presence and absence of the conductive object and controlling the transfer of energy based on a difference between the respective loading profiles. The method may further comprise controlling the transcutaneous transfer of energy based on a determined amount of heat dissipated by the object. The determined amount of heat dissipated by the object may be determined based on an amount of power provided to a rechargeable power source of the IMD and an amount of heat dissipated by the IMD.

These, and other techniques, will become apparent to those of skill in the art from the following disclosure.

DETAILED DESCRIPTION

Techniques are disclosed for transcutaneously transferring energy to an implantable medical device (IMD). The IMD may have a rechargeable power source coupled to a secondary coil. An external device having a primary coil positioned in proximity to the secondary coil may transfer energy transcutaneously to the secondary coil for use in recharging the rechargeable power source. Alternatively or additionally, the transcutaneously-provided energy may be used directly by the IMD to operate without the energy first being stored within a rechargeable power source.

It is desirable to limit the amount of heat lost within a patient's body during the transcutaneous transfer of energy to an IMD. If too much energy is allowed to dissipate as heat within the patient, the patient may experience discomfort. Moreover, this heat loss reduces the amount power available to be applied to the recharging process and/or for use by the IMD. This may slow the rate of recharge and/or reduce power available to the IMD.

The amount of heating that will occur during the transcutaneous transfer of energy is determined by a number of different factors. The amount of heat dissipated by the IMD itself will be determined based on the design of the IMD, including the amount and type of metal in the shield, and the shape, surface area, and thickness of the shield. These are known design parameters that can be taken into account when limiting the amount of energy transcutaneously delivered to the IMD.

The amount of heating occurring during energy transfer may also be affected by other conductive objects that are in proximity to the IMD when energy is being transferred to the IMD. For purposes herein, conductive objects are objects that are formed of a material such as a metal or semiconductor such that they are electrically conductive when placed within an electromagnetic field. Transfer of energy to an IMD could cause inductive heating of nearby conductive objects such as bone screws or plates, artificial body parts (e.g., hips, joints, etc.), or other IMDs (e.g., electrical stimulation or drug delivery devices) to unacceptable temperatures. Because an increasing number of patients carry multiple IMDs and other conductive objects, some of which are rechargeable or otherwise configured to receive energy transcutaneously, it is important to transfer energy to an IMD in a manner that will not cause undue heating of surrounding conductive objects.

Figure 1:
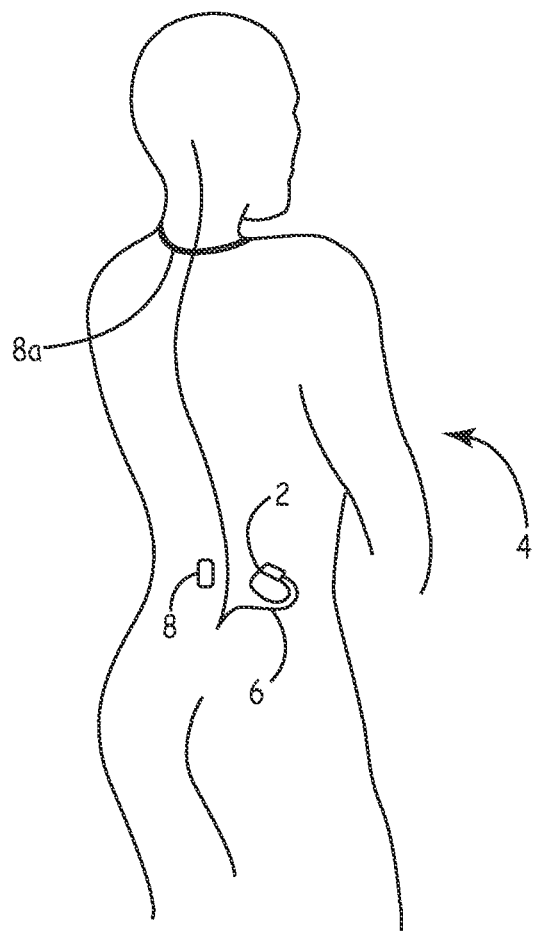
FIG. 1 is a diagram illustrating an exemplary implantable medical device.

FIG. 1 shows an exemplary IMD 2 that may take advantage of techniques disclosed herein. IMD may be adapted to deliver a type of therapy to the patient, which may include electrical stimulation and/or drug therapy. Many types of implantable medical devices may utilize the disclosed systems and techniques, including implantable therapeutic substance delivery devices, drug pumps, cardiac pacemakers, cardioverters or defibrillators, and/or devices to deliver electrical stimulation pulses for a neurological or muscular condition. Other specific examples include devices to provide therapy to treat chronic pain, tremor, Parkinson's disease, epilepsy, urinary or fecal incontinence, sexual dysfunction, obesity, or gastroparesis. Such therapy may be delivered via one or more therapy connections 6, which may be one or more leads and/or catheters.

The patient's body may carry an additional object 8 that may be an IMD that is similar to, or different from, IMD 2. For instance, object 8 may include one or more bone screws or plates, artificial body parts such as artificial hips, shoulders, and then like surgical staples or other objects. Such objects may, but need not be, implanted. For instance, metallic medical devices may be worn or otherwise carried on the exterior of the patient's body. Still other objects worn on the patient's body, such as is exemplified by object 8a, may include medical monitors, external stimulation devices and/or pumps, and so on. Object 8a could additionally or alternatively comprise non-medical objects such as jewelry, belt buckles, metal electronics carried in pockets, and so on, that may likewise be carried by the patient. Any such one or more objects that will conduct current when placed within an electromagnetic field may affect recharge and are ideally taken into account during a recharge session that recharges a recharge power source within IMD 2. Thus, the conductive object discussed herein may be a collection of one or more objects (such as objects 8 and 8a of FIG. 1) that are positioned in, and/or on, one or more locations of the body and which may be electrically conductive in the presence of an electromagnetic field. It will be understood that while reference is hereinafter made to "object 8" as being the additional conductive object, this is for brevity only, and object 8 could instead or additionally include any of one or more conductive objects considered within the scope of this disclosure.

Figure 2:
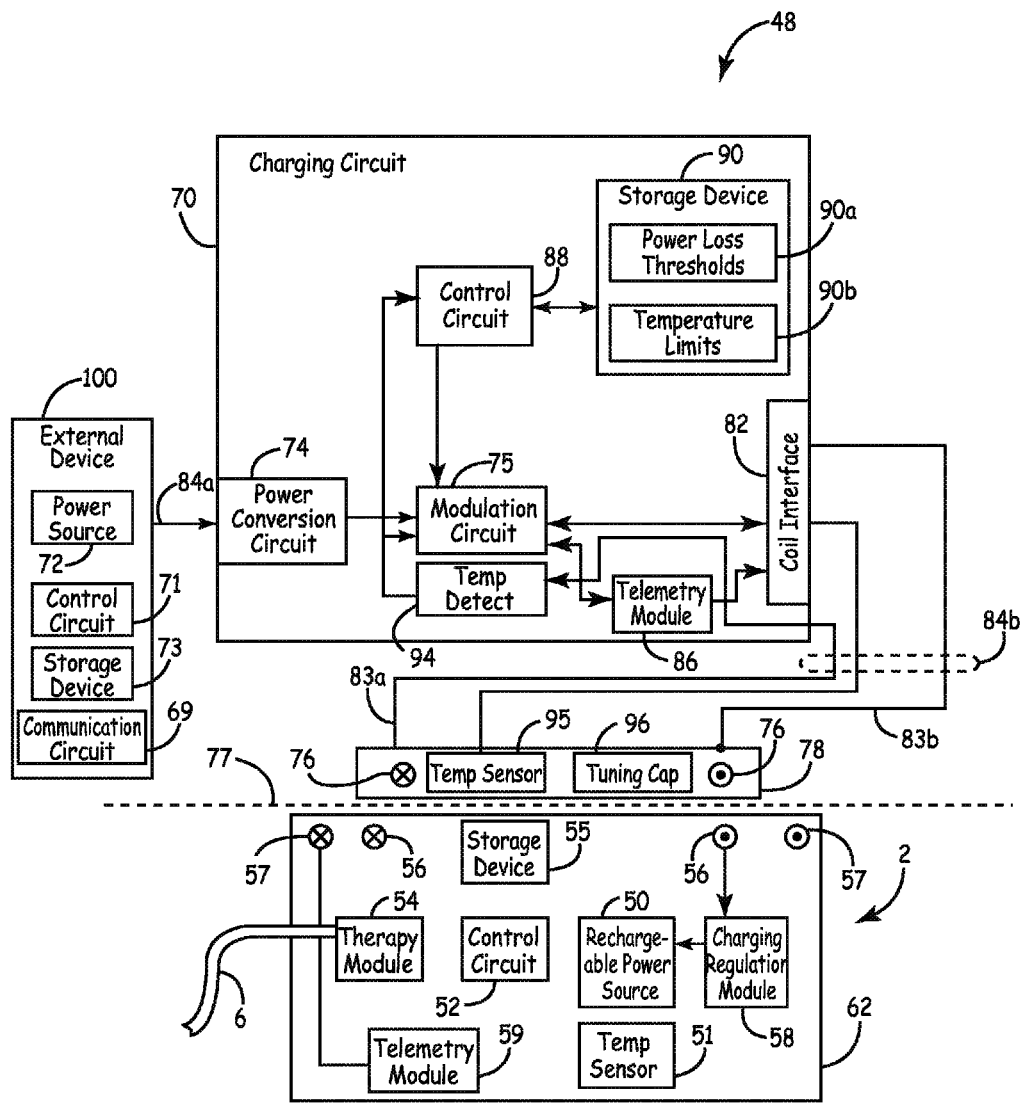
FIG. 2 is a block diagram of one embodiment of the implantable medical device of a system for recharging a power source of the implantable medical device.

FIG. 2 is a block diagram of an example system 48 that may usefully employ one or more of the techniques disclosed herein to recharge IMD 2. IMD 2 includes a rechargeable power source 50. Rechargeable power source 50 may include one or more capacitors, batteries, and/or other energy storage devices. In one embodiment, rechargeable power source 50 is a lithium ion battery. Any other type of rechargeable power source suitable for powering an IMD may be used in conjunction with the mechanisms of the current disclosure.

Rechargeable power source 50 may deliver operating power to the components of IMD 2. In some examples, rechargeable power source 50 may include a power generation circuit to produce the operating power. Rechargeable power source 50 may be configured to operate through hundreds or thousands of discharge and recharge cycles. Rechargeable power source 50 may also be configured to provide operational power to IMD 2 during the recharge process. In some examples, rechargeable power source 50 may be constructed with materials to reduce the amount of heat generated during charging. In other examples, IMD 2 may be constructed of materials that may help dissipate generated heat at rechargeable power source 50, charging regulation module 58, and/or secondary coil 56 over a larger surface area of the housing of IMD 2.

IMD 2 may also include therapy module 54, which delivers some form of therapy to a patient. This therapy may include controlled delivery of a substance and/or electrical stimulation. For example, in one embodiment, therapy module 54 may include one or more output pulse generators such as capacitive elements, voltage regulators, current regulators, voltage sources, current sources, and/or switches that are coupled directly or indirectly to rechargeable power source 50. Therapy module 54 may deliver electrical pulses to patient 4 via a combination of electrodes. As shown in FIG. 2, therapy module 54 may be coupled to patient 4 through one or more therapy connections 6 such as leads and/or catheters. Alternatively or additionally, the can of IMD 2 may carry or otherwise provide one or more electrodes for delivering therapy.

IMD 2 may wirelessly communicate with and/or control one or more other implantable devices (e.g., microdevices) within the patient's body that likewise provide therapy and/or obtain sensed signals.

Control functions for IMD 2 may be provided by control circuit 52. Control circuit 52 may include one or more processors, application-specific integrated circuits (ASICs), digital signal processors (DSPs), field-programmable gate arrays (FPGAs), discrete electronic components, state machines, sensors, memory, and/or other circuitry. The functions attributed to processors described herein may be embodied in software, firmware, hardware or any combination thereof. Control circuit 52 may, for instance, provide at least some control over operation of therapy module 54, such as by executing programs that are used to deliver stimulation according to parameters associated with those programs. Control circuit 52 may further provide functionality needed during recharging of rechargeable power source 50 as described herein. For instance, control circuit 52 may have capability to determine current and/or voltage provided to power source 50 during recharge so that power being provided to the power source may be determined.

In one embodiment, rechargeable power source 50 may be coupled to a secondary coil 56 (shown in cross-section). In some embodiments, such coupling may be accomplished via a charging regulation module 58. During a recharge session, a current is induced in secondary coil 56 which may be provided to charging regulation module 58 which may control the charging of rechargeable power source 50. Charging regulation module may be capable of monitoring current and/or voltage provided to power source 50, either alone or in combination with control circuit 52.

IMD 2 may also include a telemetry module 59 coupled to a coil such as dedicated telemetry coil 57 (shown in cross-section) or alternatively to coil 56. Telemetry module 59 may utilize various types of telemetry protocols to communicate via a coil to which it is coupled. Communication may occur with external charging circuit 70 and/or external device 100, for example. Examples of information provided to charging circuit 70 and/or external device 100 may include a charging voltage, current, and/or power delivered to power source 50 during charging.

As discussed above, telemetry module 59 may be configured to utilize various telemetry protocols. A proximity protocol may be utilized for telemetry distances of around 5 centimeters or in some cases, even longer distances. An arm's length telemetry protocol may be employed for distances of up to 1 meter. This latter type of system may utilize the electric field (E-field) component of a propagating wave to transmit information (e.g., the MICS band set aside for medical device telemetry.) Arm's length telemetry may also be achieved using the magnetic (H-field) component or coupled-coil transmission. Distance telemetry systems using E-field communication may be employed when separations between the antenna and the target device exceed arm's-length.

IMD 2 may comprise one or more storage devices such as storage device 55 for use in storing programs and patient data, for instance. Such stored data may include waveforms, thresholds, modeling data, data describing characteristics of the IMD, data describing characteristics of object 8, loading profiles that describe loading characteristics of the system when energy is being transferred to IMD, positional maps that indicate power characteristics of the system as it relates to a relative positioning between IMD 2 and an external antenna such as antenna 78 of FIG. 2, and other data that may be used to determine heating of the IMD so that heating attributable to object 8 may be determined according to various techniques described herein.

Control circuit 52 may further have the capability to monitor temperature of IMD 2, as through the use of one or more temperature sensors 51. Temperature sensors 51 may be oriented to measure the temperature of a component (e.g., secondary coil 56, power source 50, charging regulation module 58, and/or the housing of IMD 2). Temperature sensors 51 may be disposed internal of the housing of IMD 2. Temperature readings may be telemetrically communicated to charging circuit 70. Control circuit 52 of IMD 2 and/or control circuit 88 of charging circuit 70 may use these temperature measurements as feedback to control the power levels used during the charging session. Although a single temperature sensor may be adequate, multiple temperature sensors may provide more specific temperature readings of separate components or different areas of the housing. Although control circuit 52 may continually measure temperature using temperature sensors 51, control circuit 52 may conserve energy by only measuring temperature during recharge sessions. Further, temperature may be sampled at a rate necessary to effectively control the charging session, but the sampling rate may be reduced to conserve power as appropriate.

The various example components shown in conjunction with IMD 2 may be contained in a hermetically sealed housing 62. Alternatively, secondary coil 56 may be attached to, or positioned on, an exterior surface of sealed housing 62, or may be umbilically-coupled to the IMD via a cable. In one embodiment, a magnetic shield may optionally be positioned between secondary coil 56 and other electronics to substantially increase the amount of energy captured by the secondary coil and protect the electronics from electromagnetic energy when secondary coil 56 is utilized to charge rechargeable power source 50 or to other provide energy to circuits of IMD 2.

IMD 2 may also include one or more sensors such as temperature sensor 51. Temperature sensor 51 can be used to ensure that heat dissipation does not exceed predetermined limits during recharge, for instance. Other sensors might include sensors to determine a position of IMD 2 in three-dimensional space, such as three-axis accelerometers or gyroscopes. Such sensors may be used to determine a relative position between IMD 2 and an antenna being used to transcutaneously transfer energy to IMD 2. This is discussed further below.

As previously described, FIG. 2 further illustrates an example system 48 for transcutaneously transferring energy to IMD 2 (e.g., to recharge rechargeable power source 50 or otherwise provide energy for operation). System 48 includes a charging circuit 70 that may receive power from a power source 72. The power from this power source may be provided to power conversion circuit 74, which may supply appropriate power levels to modulation circuit 75.

Modulation circuit 75 may be a signal generator to generate an energy transfer signal (also referred to herein as "recharge signal") of a desired frequency, typically somewhere between 8 KHz and 500 KHz. In one embodiment, modulation circuit 75 comprises a drive circuit to drive the primary coil 76, which may be an H-bridge circuit or a signal generator, for instance. The recharge signal may be a sine wave or some other type of signal, if desired. The frequency of the recharge signal may depend on the resonant frequency of the system, which takes into account the loading placed on the system when secondary coil 56 is coupled across cutaneous boundary 77 (shown dashed) to primary coil 76. While the current disclosure primarily discusses the two coils being inductively coupled, any type of wireless energy transfer between the two coils may be used in the alternative. The frequency of the recharge signal may be varied during a charging session to find the resonant frequency of the system which will result in optimal charging efficiency. In one example embodiment described herein, the resonant frequency is substantially around 41 KHz.

The frequency of the energy transfer signal may also be varied to determine loading characteristics (e.g., a loading profile) of the system when energy is being transferred to IMD. This loading profile can be used to control the transfer of energy to the IMD 2, as will be discussed further below.

The signal generated by modulation circuit 75 may be provided to drive primary coil 76 via coil interface 82 and signal lines 83a and 83b. Primary coil 76 may be of many different configurations. The size, shape, and number of turns of the coil will generally be selected based on the size and shape of secondary coil 56, as well as the implant scenario associated with IMD 2. For instance, primary coil 76 may be selected to be of a similar size and shape as secondary coil 56. This will generally result in better inductive coupling between coils and will typically provide better energy transfer to the rechargeable power source 50.

The number of turns of the primary coil 76 may be selected based on the likely implant depth and orientation of the IMD within a patient. For instance, if IMD 2 will likely be employed in an implant scenario involving a deep or angled implant, or if the coils are to be retained at some distance from cutaneous boundary 77 during recharge, it may be desirable to utilize a primary coil having an increased number of turns, which, in turn, will increase the magnetic field produced by this coil when the coil is driven with a given input signal. This increases magnetic field strength, as may be necessary to achieve adequate inductive coupling between the primary coil 76 and the secondary coil 56 in these types of situations. A larger number of turns may likewise be needed if primary coil 76 is intended for placement at some distance from cutaneous boundary 77 instead of being placed directly on this boundary, as may be applicable for some implant scenarios. For instance, this may be the case when an insulator or a cooling device is positioned between the primary coil 76 and the cutaneous boundary 77.

The configuration selected for primary coil 76 (e.g., size, shape, number of turns) will determine the inductance of the primary coil. In one specific embodiment, the inductance of primary coil is between 1.2 and 1.3 millihenries. This inductance, along with the capacitance and resistance of the system will, in turn, affect the resonant frequency at which the system is most efficiently driven. To tune the system so that this resonant frequency is at, or near, some predetermined desired resonant frequency, a tuning capacitor 96 having a selected capacitance may be electrically coupled to coil 76. For instance, this tuning capacitor may be coupled in series or in parallel with coil 76. In one example, tuning capacitor 96 may be a 12 nanofarad (nF) capacitor, thereby resulting in a self-resonant frequency of the antenna that is nominally 41 KHz. Of course, many other frequencies may be selected as the resonant frequency with the value of the tuning capacitor 96 being selected accordingly as is known in the art.

Coil and tuning capacitor 96 may be housed within an antenna 78, which may be a structure made of a material that is an electrical insulator. For instance, it may be made of a polymer that has a comfortable texture suitable for placement against the skin of the patient. Various types of polymers, including silicones, polypropylene, and urethanes may be used for this purpose. In one embodiment, antenna 78 is made of a thermally-conductive elastomer material that is capable of spreading heat generated by coil 76 over a wider surface to increase patient comfort during recharge.

In some examples wherein tuning capacitor 96 is coupled in series with coil 76, when coil 76 is being driven with an oscillating signal, as will occur during recharge, node 166 electrically coupling capacitor 96 to coil 76 will "ring up" to a high amplitude voltage. Positioning the tuning capacitor 96 within antenna 78 will ensure that this high-voltage node is well insulated by the electrically-insulating material used to form antenna. An alternative embodiment may locate tuning capacitor 96 within circuit 70 that is situated remotely from antenna 78. This would place the high-voltage node within interface 84b (shown dashed), which may not be desirable if a cable that embodies this interface is damaged. Such a scenario may pose a shock risk. Thus one embodiment places tuning capacitor 96 within antenna 78 to avoid risk of shock.

Charging circuit 70 may have a telemetry module 86 enabling communication with IMD 2 during a charging session to provide status or other information concerning the charging session. In some examples, telemetry module 86 receives information that may include voltage, current, and/or power levels associated with power source 50 during recharge, temperature measurements obtained from temperature sensor 51, positional measurements obtained from sensors such as three-axis accelerometers, and/or other measurements, data and status employed according to techniques described herein.

Telemetry module 86 may be adapted to utilize various types of telemetry protocols, including a proximity protocol for telemetry distances of around 5 centimeters or less, and an arm's-length telemetry protocol for distances of up to, or even exceeding, 1 meter. In one specific embodiment, telemetry module 86 is adapted to utilize a proximity protocol to communicate with IMD 2 via primary coil 76. Secondary recharge coil 56 may be used to transmit/receive such a communication to/from primary coil 76. Alternatively, a dedicated telemetry coil such as telemetry coil 57 may be provided within IMD 2 for this purpose, as previously described.

In one embodiment, charging circuit 70 may be automatically activated using a telemetry signal received from IMD 2. For instance, charging circuit 70 may continuously send out requests via telemetry communication. When IMD 2 is in proximity to rechargeable power source 50, IMD 2 may send an acknowledgement to these requests so that charging circuit 70 may automatically initiate a recharge session without user intervention. Alternatively, the recharge session may be initiated upon user request or some other interaction between IMD 2 and charging circuit 70.

One or more functions performed by charging circuit 70 may be controlled by control circuit 88. For example, control circuit 88 may automatically provide control signals to indicate how modulation circuit 75 is to drive primary coil 76. Control circuit 88 may include one or more processors, FPGAs, ASICs, DSPs, microsequencers, discrete components, and/or other electronic circuit components to perform such functions. The term "processor" or "processing circuitry" may generally refer to any of the foregoing logic circuitry, alone or in combination with other logic circuitry, or any other equivalent circuitry which may, but need not, include storage devices such as embedded memory devices.

Some or all of the functionality ascribed to control circuit 88 may be embodied or encoded in instructions stored within a non-transitory computer-readable medium such as storage device 90. The term "non-transitory" may indicate that the storage medium is not embodied in a carrier wave or a propagated signal. However, the term "non-transitory" should not be interpreted to mean that storage devices 90 are non-movable. As one example, storage device 90 may be removed from charging circuit 70, and moved to another device. In certain examples, a non-transitory storage medium may store data that can, over time, change (e.g., in RAM).

Storage device 90 may include volatile, non-volatile, magnetic, optical, and/or electrical media for storing digital data and programmed instructions, including random access memory (RAM), read-only memory (ROM), non-volatile RAM (NVRAM), electrically erasable programmable ROM (EEPROM), flash memory, removable storage devices, and the like. In some implementations, charging circuit 70 may include a device interface that provides for transfer of data from charging device 70 to another device for storage. For example, charging device 70 may store data on a networked storage device through a network interface, or to a local storage device using a universal serial bus (USB) interface. Such storage devices may store instructions to cause control circuit 88, which may include a programmable processor, to perform one or more methods such as those described herein. This operation may occur either alone, or in conjunction with, operation of control circuit 52 of IMD 2 and control circuit 71 of external device 100.

According to one embodiment, storage device 90 and/or one or more other storage devices within the IMD 2, external device 100, or somewhere else within the system may store data used to control transcutaneous transmission of energy. Such data may include, but is not limited to, power loss thresholds 90a and temperature limits 90b. Other examples of data stored by storage device 90 may include such things as loading profiles and positional maps that are used to determine how heat is being dissipated by IMD 2 and object 8. This will be discussed further below in conjunction with description of control of the transfer of energy to IMD 2 as may occur during a typical recharge session.

In one embodiment, charging circuit 70 may include a temperature detection circuit 94. This circuit receives one or more signals from at least one temperature sensor 95 that may be carried by antenna 78 and is in proximity to coil 76. Temperature sensor 95 provides one or more signals to temperature detection circuit 94 to allow the charging circuit 70 to determine whether temperature limits are being met during recharge. Such limits may be based on government regulations, patient preferences, and/or some other standard, and in some cases may be user-selectable (e.g., programmably selectable by a clinician or patient). If a detected temperature is exceeding a predetermined limit, temperature detection circuit 94 may provide a signal to control circuit 88. This may cause control circuit 88 to alter the signal driving the antenna 78 so that the temperature of the antenna will be reduced to within acceptable limits.

Charging circuit 70 receives energy from a power source 72, which in one embodiment, may be selectable by the user to be any one or more of an AC wall outlet, rechargeable batteries (e.g., lithium ion batteries) and/or prime cell batteries. Such batteries may be housed with charging circuit or housed in a separate device.

In the illustrated scenario, the power source is power source 72 that is housed within an external device 100. This external device 100 may be a patient or clinician programmer used to exchange data (e.g., programming commands, patient information, status information, etc.) with IMD 2 and/or provide recharge capabilities. In one example, external device 100 provides some control during transfer of energy to IMD 2. For instance, external device may modulate the level of energy provided by charging circuit 70 to IMD 2 to limit tissue heating, as will be described below.

External device 100 may be coupled to charging circuit 70 over interface 84a. This interface may be a cable that removably plugs into a connector of the external device. Such a configuration allows charging circuit 70 and coil 76 to be removably coupled to the external device 100. The connector provided for this purpose may be designed according to an industry-standard (e.g., Universal Serial Bus standard) or may be a proprietary-type connector.

External device 100 may include a control circuit 71 comprising one or more processors, Application Specific Integrated Circuits (ASICS), state machine logic, software, firmware, and/or any type of logic known in the art. Control circuit 71 may provide some level of control to charging circuit 70 in one embodiment. As discussed above in regards to control circuit 88, this control circuit may perform one or more of the techniques described herein either alone, or in conjunction with, operation of control circuit 88 or control circuit 52.

External device 100 may further include a storage device 73 for storing programmed instructions such as firmware and/or software, control parameters, patient data, programming parameters to control operation of IMD 2, and any other instructions and/or data needed to aid in control of charging circuit 70, IMD 2 and/or external device 100. For instance, in some examples, instructions stored within storage device 73 may control execution of control circuit 71. Storage device 73 may include one or more volatile, non-volatile, magnetic, optical, and/or electrical media for storing digital data and programmed instructions, including random access memory (RAM), read-only memory (ROM), non-volatile RAM (NVRAM), electrically erasable programmable ROM (EEPROM), flash memory, removable storage devices, and the like.

External device 100 may also include a communication circuit 69 for communicating with telemetry module 59 of IMD 2 and/or telemetry module 86 (as may be desirable when external device 100 is not coupled via interface 84a to charging circuit 70). In one example, communication circuit 69 may provide short-range inductive telemetry and/or longer range RF telemetry.

Communication circuit 69 may further provide the capability to communicate with another external device such as a recharger, a programmer or computing device via a wired or wireless connection using any of a variety of local wireless communication techniques, such as RF communication according to the IEEE 802.11 or Bluetooth® specification sets, infrared (IR) communication according to the IRDA specification set, or other standard or proprietary telemetry protocols. Further, external device may communicate via a local area network (LAN), wide area network (WAN), public switched telephone network (PSTN), or cellular telephone network, for example.

In some implementations, external device 100 may include a device interface that provides for transfer of data from the external device 100 to another device for storage. For example, external device 100 may store data on a networked storage device through a network interface, or to a local storage device using a universal serial bus (USB) interface. In this manner, external device 100 may also communicate with other programming or computing devices via exchange of removable media, such as magnetic or optical disks, or memory cards.

It will be understood that the system shown in FIG. 2 is illustrative only. External system 48 may take other forms. For instance, one or more of the components shown housed in antenna may instead be housed in charging circuit 70. In one embodiment, antenna 78 may be eliminated, with primary coil 76 residing within the housing of charging circuit 70. In another embodiment, charging circuit 70 may reside in a same housing with the components of external device 100. In still other embodiments, components may be partitioned differently. For instance, communication circuit 69 may reside within charging circuit 70 or antenna 78 instead of within external device 100. Thus, many other possible configurations may be contemplated by those skilled in the art, with the configuration of FIG. 2 being illustrative only.

Figure 3:
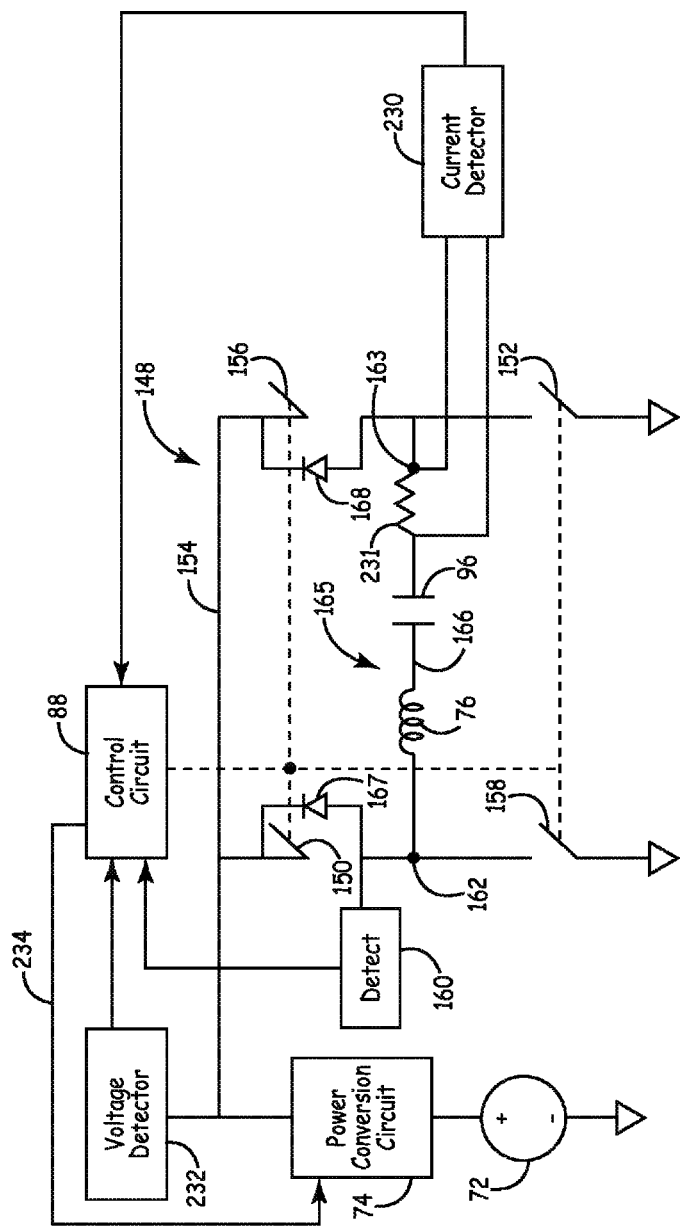
FIG. 3 is a diagram of a circuit that may be used by a charging device to drive a primary coil to transcutaneously transfer energy.

FIG. 3 is a diagram of a circuit that may be used by charging device 70 of FIG. 2 to drive primary coil 76. An H-bridge circuit 148 of the type known in the art comprises four switches 150, 152, 156, and 158, which may be Field-Effect Transistors (FETs), Micro-Electro-Mechanical (MEMs) switches, or some other type of switch controllable by control circuit 88.

The circuit includes a power source 72 and power conversion circuit 74. As previously described, power source may be a prime cell or rechargeable battery, or some other power source. In a specific example, power source 72 may provide a voltage level of between 7 and 8 volts to power conversion circuit 74. Power conversion circuit 74 is a boost circuit that may boost the voltage level received from power source 72 to a DC voltage of between 8 and 12 volts in one embodiment, which is a voltage that may be used for operation of H-bridge circuit 148.

The H-bridge circuit 148 is employed to generate a signal in the tank circuit 165, wherein the tank circuit comprises tuning capacitor 96 and primary coil 76. Specifically, control circuit 88 generates pulses to gate switches 150 and 1520N for a predetermined period of time, thereby allowing current to flow from node 154 through switch 150 and the tank circuit 165 and finally to ground through switch 152. Sometime thereafter, switches 150 and 152 are gated OFF and pulses are generated to turn switches 156 and 1580N. This allows current to flow from node 154 through switch 156 and the tank circuit 165, and finally to ground through switch 158. By generating drive signals to gate switch pairs 150, 152 and 156, 158 in this manner, the voltage at each of nodes 162 and 163 will approximate a sine wave. As noted above, the frequency of this signal will be determined based on the self-inductance of the tank circuit 165 as well as the mutual inductance of the system that additionally comprises the secondary coil 56 of the IMD.

The duty cycle of each switch pair cannot exceed 50%, since only one switch pair can be driven at a time without shorting power to ground. In fact, each switch pair must be driven at a duty cycle of somewhat less than 50% because the transition between closing one switch pair and opening another cannot occur simultaneously. To allow sufficient time for one switch pair to become non-conducting before gating another switch pair ON, there is an enforced "dead period" of time during which none of the switch pairs allowing current to flow. During this dead period, at least one side of the tank circuit 165 is "floating", being coupled neither to ground nor to power. During this time, a "fly-back" voltage develops at a floating node of the circuit, which may be either node 162 or 163. In one embodiment, the amplitude of this fly-back voltage may be held to some predetermined maximum voltage by diodes 167 and 168 that are provided across switches 150 and 156, respectively. In another embodiment wherein FETs are used for the switches 150, 156, diodes 167 and 168 may be eliminated and the body diodes of the FETs may be relied upon to limit voltage at nodes 162 and 163. In yet another embodiment, both the body diodes of the FETs and additional diodes 167 and 168 may be used for this purpose.

If the tank circuit is driven at the resonant frequency of the system, current flowing through tank circuit 165 will be in phase with the voltage across the tank circuit. In other words, the phase angle between the tank voltage and the tank current will be zero. When this is the case, power losses are minimized.

In one embodiment, detect circuit 160 is used to provide feedback to control circuit 88 so that voltage and current remain substantially in-phase. The details of detect circuit are beyond the scope of this disclosure and are described in detail in provisionally-filed patent application Ser. No. 61/476,584 filed Apr. 18, 2011 entitled "Recharge Tuning Techniques for an Implantable Device" which is assigned to the assignee of the current disclosure, the contents of which are incorporated herein by reference to the full extent that such disclosure is not inconsistent with the current disclosure.

The circuit of FIG. 3 may include a current detector 230 to sense the current through tank circuit 165 by measuring voltage across resistor 231. In one embodiment, current detector 230 detects the peak current level through the tank circuit, but current detector 230 may measure a different current level in other embodiments (e.g., root-mean-square (RMS) current value, etc.) The monitored current level may be provided to control circuit 88.

FIG. 3 may also comprise a voltage detector 232. This voltage detector may monitor the voltage level being provided by power conversion circuit 74 at node 154. This voltage level is adjustable based on signal 234 provided by control circuit 88.

Whereas an embodiment of an H-bridge circuit for generating a signal in tank circuit 165 is described, many other types and configurations of drive circuits are available for this purpose. For instance, a signal generator (e.g. a sine or square wave generator) may be used for this purpose.

The circuit of FIG. 3 may be employed to calculate heat dissipated within the system as follows. As discussed above, during recharge, power is delivered to primary coil 76 by charging circuit 70. This power is used to transfer energy to IMD 2. A portion of this transferred energy is used to recharge rechargeable power source 50, and another portion of this transferred energy may be dissipated within IMD 2 as heat. Still another portion of the total amount of energy delivered to primary coil 76 may be transferred to another electrically-conductive object 8 (FIG. 1) that is in proximity to IMD 2 during recharge. For purposes herein, "proximity" means that object 8 is close enough to IMD 2 to receive some of the energy transferred transcutaneously to IMD 2 by antenna 78 (e.g., during a recharge session when power source 50 is being recharged.) This can result in heating of conductive object 8.

Object 8 may include other implantable medical devices or objects (e.g., bone screws, other stimulator or drug delivery devices, etc.), externally-worn medical devices, and/or externally worn non-medical objects such as jewelry or belt buckles. Any type of electrically-conductive object that is close enough to IMD 2 to receive power during recharge may be subject to heating and is optimally taken into account when recharging rechargeable power source 50.

According to one aspect of the disclosure, the total amount of heat dissipated by IMD 2 and object 8 may be determined using several values that are either known or can be determined within the system. For instance, it is known that of the total power that is supplied to the primary coil ("Power_Primary"), at least some of this power may be used to recharge power source 50 of IMD 2 ("Power_Charge") assuming the primary coil 76 and secondary coil 56 are sufficiently oriented to allow this to occur. Some power will be lost to heat that is dissipated in the primary coil ("Heat_Primary"). The rest of the power is lost as heat in the IMD 2 or within conductive object 8 ("Heat_IMD" and "Heat_CO", respectively). This relationship may be represented as follows:

Heat_IMD+Heat_CO=Power_Primary−Heat_Primary−Power_Charge  (Equation 1)

Assuming both the voltage and current in primary coil 76 are sine waves, the value for Power_Primary is the product of the RMS current in the primary coil, the RMS voltage across the primary coil, and the cosine of the phase angle between these two signals. The RMS current in the primary coil may be determined directly by dividing the peak current in the coil, which is measured by current detector 230, by the square root of two. In one example, the RMS voltage in the primary coil may be determined as follows:

$$V_{rms} = \text{Voltage} \sqrt{\frac{2W}{1/freq}} \quad \text{(Equation 2)}$$

In this equation, "Voltage" is the voltage at node 154 provided by power conversion circuit 74, "W" is the width of a pulse used to gate one of the switch pairs ON (either switches 150 and 152 or switches 156 and 158), and "freq" is the drive frequency of the H-bridge circuit. The pulse width "W" and the drive frequency of the H-bridge circuit are "known" values available to control circuit 88, which is controlling the H-bridge circuit.

Finally, the phase angle between current and voltage must be determined. In one example, it may be assumed that after frequency tuning has been performed, the phase angle between RMS current and RMS voltage is zero such that the cosine of the phase angle is "one". In another example, the phase angle may instead be measured to achieve more accuracy. This can be accomplished by comparing the timing of a signal at node 162 of the H-bridge circuit, as may be determined by detect circuit 160, to a zero crossing of the tank current waveform as indicated by current detector 230. To increase accuracy of this phase difference determination, calibration may be performed to ensure that delay imposed by detect circuit 160 is substantially the same as delay imposed by current detector 230.

Using the foregoing technique, the power delivered to primary coil 76 may be determined as the product of the RMS current in the primary coil, the RMS voltage across the primary coil, and the cosine of the phase angle between these two signals.

As discussed above, some heating will occur in the primary coil. This value for Heat_Primary is the product of the square of the RMS current in the primary coil (as determined by current detector 230) and a known system constant value for the AC series resistance of primary coil 76 itself at the nominal resonant frequency, which in this example is 41 KHz (absent of any contribution from loading because of coupling between the primary and secondary coils). This AC series resistance is a constant value that may be empirically determined or calculated using mechanisms known in the art, for instance.

One way to measure the AC series resistance is to drive the primary coil at the resonant frequency of the coil in the absence of IMD 2 and conductive object 8. While the primary coil is being driven in this manner, the value for Power_Primary may be determined using techniques described above. This value for Power_Primary may be divided by the square of the RMS current in the primary coil, which is determined using techniques described above. This will yield the value for the AC series resistance measured at the resonant frequency of the system. This value may be stored for later use in determining Heat_Primary.

Once the value for the AC series resistance of primary coil 76 has been obtained, a value for Heat_Primary may be determined based on a given current level in the primary coil. Control circuit 88 may use this value to ensure that the value of Heat_Primary does not exceed patient preference and/or regulatory limits. For instance, control circuit 88 may ensure that the RMS current in the primary coil 76 does not exceed some predetermined maximum value such that a threshold value for Heat_Primary is exceeded.

Another value that may be determined is the amount of power delivered to charge rechargeable power source 50 of IMD 2, Power_Charge. This value may be determined as a product of the voltage delivered to rechargeable power source 50 and the recharge current delivered to the power source, both of which may be measured by a circuit (e.g., charging regulation module 58) of IMD 2. In one embodiment, these measured values may be provided via telemetry module 56 to charging circuit 70. In some embodiments, the voltage associated with rechargeable power source 50 will remain substantially constant during most of a recharge session (e.g., until battery "top off" occurs). The value for the battery voltage level will therefore be a known value. As such, only the current to power source 50 need be measured to determine Power_Charge.

Using Equation 1 set forth above, the amount of heat dissipated collectively by both IMD 2 and object 8 may be determined. Specifically, this is determined by subtracting Power_Charge from the total amount of power delivered to IMD 2 and object 8 (i.e., Power_Primary−Heat_Primary). In one embodiment, control circuit 88 may then adjust power delivered to primary coil 76, Power_Primary, by adjusting the voltage and/or duty cycle used to drive the H-bridge circuit so that power being provided by primary coil 76 to IMD 2 and object 8 is reduced. This manner in which the voltage and/or duty cycle is varied may be based on the amount by which the amount of heat dissipated collectively by both IMD 2 and object 8 exceeds an associated power loss threshold. For instance, an amount by which a power loss threshold is exceeded may be used to reference a look-up table. This referenced table may provide a new value for the duty cycle and/or voltage to be used in controlling the H-bridge circuit such that power provided by primary coil 76 is reduced, and in turn, the heat dissipation value no longer exceeds the threshold. This is described in more detail in reference to FIG. 4A below.

If desired, the amount of heat dissipation attributable individually to each of IMD 2 and object 8 may be determined as follows. The amount of power lost as heat within IMD 2, or "Heat_IMD", is the result of several key factors. First, power may be lost as heat because of the current flowing during the recharge operation. This current may comprise the recharge current flowing into the battery as well as any shunt current that may be shunted away from the battery to prevent a battery overcharge condition. In one embodiment, both of these values are measurable within the IMD and can be communicated via telemetry to system 48 to derive an estimate of the power lost as heat because of the flow of these currents during recharge.

Another source of power loss to heat within IMD 2 is the result of normal circuit operations of the IMD that are performed to accomplish the functions attributable to the IMD. The amount of power loss to this normal operation may vary somewhat depending on the type of operations occurring at a given instant in time. Such operations may include sending and/or receiving a telemetry transmission, storing/retrieving a block of data or instructions from memory, processing-intensive operations related to monitoring physiological signals, therapy delivery functions, and so on. While the type of operation may affect the precise amount of power lost to normal circuit operations at a given time, an estimate of average power loss attributable to typical circuit operations can be determined empirically or calculated based on design specifications for a given system.

In one example, a more precise estimate of heating based on circuit operations may be determined based on the known set of operations that are taking place at a given moment in time. For example, a look-up table may store types of functions performed by the IMD, each being associated with a previously-measured value for power lost while conducting this type of function for a predetermined period of time. Using such information, an accurate estimate of the power lost during various circuit operations can be obtained for a specific type of design. IMD 2 may transmit information to charging circuit 70 indicating types of operations occurring at a given time to allow charging circuit to derive such an estimate, or control circuit 52 of IMD may derive such an estimate, which is then transmitted to charging circuit.

In still other embodiments, a Coulomb Counter may alternatively or additionally be employed to determine current being provided from power source 50 to the circuits of IMD for use in determining an amount of heating attributable to functions occurring within IMD 2 at a given time. Again, this information may be transmitted to charging circuit 70 for use in deriving a value for Heat_IMD or may be used by IMD 2 to estimate the heat value.

Still another source of power lost to heating within the IMD relates to eddy currents that are induced in the IMD shield (or "can") during recharge operations. Assuming the IMD has a "typical" orientation wherein a major plane of the IMD's surface is parallel to a cutaneous boundary of the patient, the amount of heat losses in the shield during recharge will be proportional (e.g., based on a constant K) to the sum of the recharge current and any shunt current. As previously discussed, the recharge and shunt currents may be measured within the IMD in one embodiment and provided via telemetry to system 48, as discussed above. The value of constant K may be determined empirically (e.g., by actually measuring heating as well as the recharge and shunt currents during recharge while the shield is in a controlled environment). Alternatively, a value for constant K may be determined using modeling techniques, wherein the model takes into account such factors as the thickness, shape, surface area, and materials used to construct the shield. In general, shield losses are proportional to shield thickness and inversely proportional to the resistivity of the shield materials.

As noted above, the orientation of the shield may affect the shield losses since if a major plane of the device is not substantially parallel to a cutaneous boundary of the patient, flux lines will intersect with the IMD obliquely, contacting the side walls of the shield. "Typical" eddy currents may not be induced within the shield in this type of scenario. Further, because most flux lines will not be coupled to the secondary coil, the recharge current may be smaller than expected. For these reasons, in scenarios where the IMD is not substantially parallel to a cutaneous boundary, different values of K may be used. These values may be determined empirically be positioning the IMD in a controlled environment (e.g., a gel bath that simulates the human body) at various angles with respect to a pseudo-cutaneous boundary so that heating can be measured while antenna 78 supplies energy to IMD 2. Such values may likewise be determined using known modeling techniques, wherein the model is adjusted to take into account the angled-implant scenario.

After one or more values for constant K have been determined in any of the aforementioned ways, the values may be stored for later use. For instance, these values may be stored in a table along with information that describes, for each value of K, the associated implant scenario corresponding to that value (e.g., coil orientation and implant depth). After IMD 2 is implanted, the appropriate value for constant K may then be selected for use based on the implant scenario, if appropriate. This value may be programmed into the IMD and/or an external device for use in determining the eddy losses.

In addition to storing one or more values for a constant K, other information may be stored for use in performing recharge. As an example, an angled-implant scenario may pose a challenge when attempting to establish a recharge session. For instance, it may take the patient longer to locate antenna 78 in a position wherein the recharge current flowing into power source 50 is considered "good enough" to sustain a recharge session. The IMD may provide feedback via telemetry communication indicating that the patient needs to continue re-positioning antenna 78 until at least some minimum level of recharge current is flowing to power source 50. In one example, this minimum amount may be stored (e.g., along with the values for constant K) and programmably selected based on the known orientation of the IMD. This re-adjusting of the expected recharge current may prevent the patient from becoming frustrated when multiple attempts to locate antenna 78 do not result in some "expected" level of current flowing to rechargeable power source.

Other values may be stored for use in controlling a recharge session. For instance, it may be determined that the recharge current flowing to power source 50 should not be allowed to exceed some predetermined maximum value. Different maximum values may be associated with different implant scenarios, or a single maximum value may be associated with all implant scenarios. This recharge current limit may serve as another safeguard to ensure that a value for Heat_IMD will not exceed acceptable levels. This is described further below.

The various types of information discussed above, including one or more values for constant K, minimum acceptable recharge current levels and/or maximum allowable recharge current levels may be programmably stored within a storage device of the IMD 2, charging circuit 70 and/or external device 100, for instance.

In accordance with the foregoing, values for Heat_IMD may be determined based on factors such as a measured shunt current, constant values associated with shield losses, information on the amount of current being used during various types of IMD operations, and so on. Such determinations are generally product-specific may be determined empirically or using modeling techniques. Generally, a given value for Heat_IMD will be associated with a particular level of recharge current and implant scenario. Thus, lookup tables may be constructed that associate a particular recharge current level and implant scenario with an associated value for Heat_IMD. Once the recharge current level is obtained from measurements, and the implant scenario is known, an appropriate table may be referenced to determine the associated level of Heat_IMD, which may then be used as an estimate of the heating occurring within the IMD.

After the value for Heat_IMD is determined, a specific value attributable to heat dissipated by object 8 (i.e., Heat_CO) may be determined from Equation 1 above. The values for Heat_IMD, Heat_CO, and Heat_Primary may then be used to control the transfer of energy to IMD 2 to maintain heating under desirable limits.

The foregoing discusses using various constants associated with design of IMD 2 as well as various measurements taken during recharge to estimate an amount of power lost to heat within IMD 2, Heat_IMD. Another way to determine the amount of power loss attributable to heating of just IMD 2 exclusive of any object 8 is to apply the foregoing Equation 1 to a scenario wherein it is known that no other conductive object is present during recharge. For instance, if an IMD is implanted before any other object 8 is present within the patient's body and no object 8 is being carried on the exterior of the patient's body such that Heat_CO is zero, a recharge session may be conducted wherein values for Power_Primary, Heat_Primary, and Power_Charge may be obtained as described above.

A specific example of the foregoing may be considered as follows. Since Heat_IMD is largely related to the recharge current flowing to power source 50 of IMD 2 for reasons discussed above, it may be desirable to estimate a value for Heat_IMD when a particular recharge current is flowing to the power source. This may increase the accuracy of the estimate. As such, primary coil 76 is driven at a power level Power_Primary that will achieve a predetermined recharge current flowing to power source 50. Assuming that Heat_CO is zero because of the absence of a conductive object, and being able to calculate values for Power_Primary, Heat_Primary, and Power_Charge, Equation 1 may be used to determine an estimated value for Heat_IMD when the predetermined recharge current exists.

As was described above, the determined value for Heat_IMD will be associated with a given implant and recharge scenario. Specifically, the value for Heat_IMD is associated with the specific implant scenario that existed when the measurement was taken. If something occurs to change that scenario, such as the device shifts within the patient's body so that the secondary coil is now angled, the determined value for Heat_IMD may need to be re-determined. Likewise, Heat_IMD will generally be associated with a particular recharge scenario, such as the frequency and relative positions of primary and secondary coils that were in use when the recharge session was conducted to measure Heat_IMD. For instance, Heat_IMD may have been determined at the system resonant frequency when a certain alignment was known to exist between the primary and secondary coils (e.g., the coils substantially shared a central axis) and when a predetermined recharge current was being achieved. If this recharge scenario does not exist, using the predetermined value for Heat_IMD may not achieve accurate results for Heat_CO.

If desired, multiple values for Heat_IMD may be determined when various types of operations are being performed by IMD 2 while the predetermined recharge current exists. For instance, values for Heat_IMD may be determined both when telemetry transmissions are occurring, and when they are not occurring, and so on. If desired, the value for Heat_IMD that is selected for use at any given time may be based on the known operations occurring within IMD 2 at that time. Alternatively, an average of these multiple values may be determined for use as an estimate of Heat_IMD during a "typical" recharge session when the recharge current to power source 50 is at the predetermined value.

In the foregoing manner, one or more values for Heat_IMD may be determined in the absence of conductive object 8. Such values may be determined after the IMD 2 is implanted in a patient and before object 8 is present, or before IMD 2 is implanted and when IMD 2 is in a controlled embodiment (e.g. a gel bath) in the absence of object 8. In either case, each value for Heat_IMD may be associated with a given recharge scenario (e.g., recharge frequency and a value for a recharge current), a particular implant scenario (e.g., implant depth and spatial relationship between primary and secondary coils), and/or a list of which other operations are occurring within IMD 2 during the recharge session to contribute to heating. This list of operations may instead be replaced by an amount of current drawn from power source 50 as measured by a Coulomb counter. Such information may be stored within one or more lookup tables.

Later, object 8 may be implanted or otherwise positioned in proximity to IMD 2. Primary coil 76 may be driven using substantially a same recharge and implant scenario as was used when an estimate of Heat_IMD was initially obtained. For instance, the power level in the primary coil 76 (Power_Primary) may be adjusted to achieve a predetermined recharge current in the power source 50. This recharge current value, as well as aspects associated with the recharge and implant scenario, may be used to select an appropriate table for use in retrieving a corresponding value for Heat_IMD. This value for Heat_IMD may then be applied to Equation 1 to determine a value for Heat_CO.

Using the foregoing technique to estimate Heat_IMD, certain measurements and constants need not be known and/or used (e.g., values for shunt current, and constants associated with eddy currents within the shield, etc.) Instead, values for Heat_IMD are determine using measurements for current and voltage of power source 50 obtained in the absence of conductive object 8 for various implant and recharge scenarios. This may provide simplification when it is not important to analyze with more particularity how heat is being dissipated within IMD 2. Of course, in a scenario wherein it is desirable to understand the various contributing factors to Heat_IMD (e.g., heating because of shunt current versus heat absorbed by the IMD shield), it may still be desirable to use the calculations described above rather than the more empirical method to determine a value for Heat_IMD.

As previously described, values for Heat_IMD may be determined post-implant before conductive object 8 is present. In this case, certain factors associated with the implant scenario may be assumed to remain constant both before and after conductive object is present. For instance, it may be assumed that the orientation and depth of secondary coil 56 within the patient's body will not change after conductive object 8 is present, since IMD 2 remains at a relatively fixed position within the patient's body regardless of the presence or absence of object 8. However, if IMD 2 shifts position within the patient's body such that the coil orientation changes, or if the patient gains or loses weight after the values for Heat_IMD are determined, it may be necessary to measure new values for Heat_IMD.

In the case wherein values for Heat_IMD are established pre-implant prior to the presence of conductive object 8 (e.g., by placing IMD in a controlled environment such as a gel bath), it is possible to adjust the position and orientation of IMD 2 in a manner that is not possible in the post-implant example. This type of adjustment allows various values for Heat_IMD to be empirically determined for different implant depths and relative coil orientations. Various lookup tables or other data structures may be populated with this data so that an appropriate value for Heat_IMD may be obtained for use with a given implant and recharge scenario.

Yet another way to estimate power lost to heating of just IMD 2 is to utilize one or more temperature sensors such as temperature sensor 51 situated at various locations relative to the shield and circuitry of the IMD. The temperature readings obtained periodically throughout recharge can be communicated via telemetry to system 48 or used by control circuit 52 to estimate the amount of power being lost to heating of the IMD. For example, assuming the amount of power lost to heating within the IMD remains constant throughout a recharge session, the temperature of the IMD may continue to rise at a relatively constant rate throughout the recharge session. Thus, by taking into account an initial temperature prior to the time temperature began to rise, a time elapsed since temperature began to rise, and a current temperature reading, an estimate for Heat_IMD may be determined at a given point in time during recharge. If desired, readings may be taken at various times throughout the recharge session, with respective power loss estimations being based on both the temperature and the respect time (e.g., ten minutes after recharge initiation) at which the temperature reading was obtained. As was the case above, a value for Heat_CO may be determined using Equation 1 above.

Once the amount of heat individually attributable to object 8 is determined, it may be desirable to control the transfer of heat to maintain this heat dissipation value under some threshold value. The acceptable amount of power lost within this object may be based on the size, shape, location, and material used to construct the object. For instance, a relatively large component such as an artificial hip may be capable of absorbing more heat due to power losses than a small bone screw. Moreover, some materials will increase in temperature faster than other materials. Additionally, the location within the patient's body of object 8 may affect the power losses that may be tolerated. These and other factors may be used to determine a maximum amount of power lost to heat that can be associated with a given object 8. Such characteristics can be obtained through manufacturer's specifications, patient records, imagining techniques (e.g., Xray images), or some other method.

In one embodiment, a power loss threshold may be selected for object 8 such that so long as Heat_CO remains below this threshold, this object will not experience a rise in temperature at the interface between the object and tissue of greater than some predetermined temperature (e.g., about 41 degrees C.) This type of heat threshold can be determined empirically or using known modeling techniques that take into account characteristics such as those described in the foregoing paragraph.

According to one example, data descriptive of the object 8 and the amount of heat energy it may safely absorb, including any power loss thresholds 90*a* for this object, may be stored in a storage device of the system such as storage device 55 of IMD, storage device 90 of charging circuit 70 and/or storage device 73 of external device 100. The threshold value may then be retrieved from a storage device and used during energy transfer to IMD 2 to ensure that if Heat_CO exceeds this threshold, some appropriate action will be taken. As previously discussed, this may involve varying one or more parameters associated with the circuit driving primary coil 76 (e.g., duty cycle, voltage, current, etc.). In this manner, the amount of Heat_CO that may be tolerated in conjunction with object 8 may depend on characteristics of the object, including size, extent and type of surface area, location of the object within the body, type of tissue in contact with the object, location of the object with respect to IMD 2, and other characteristics associated with the object and the implant scenario.

In another embodiment, multiple thresholds may be stored in association with the same object 8. For example, a first threshold may be selected for use if the patient is willing to tolerate higher temperatures so that recharge may be completed more quickly. One or more additional thresholds may be provided for patients having lower temperature tolerances but who are willing to spend more time recharging their devices.

In yet another example, the threshold values may be based, at least in part, on the relative location between IMD 2 and object 8. For instance, if object 8 is relatively close to IMD 2 (e.g., within several centimeters), a lower heat threshold may be used for object 8 since a same relatively small volume of tissue is absorbing heat from both IMD 2 and object 8. Allowing more than this threshold amount of heat absorption to occur may result in patient discomfort. On the other hand, if object 8 is farther removed from IMD 2 (e.g., more than a few centimeters) it may be acceptable to allow a heating threshold for object 8 to be higher.

A threshold heat amount to be used for a given patient may be selectable by a clinician, patient, a manufacturer's representative, and/or some other user in one example. Thus, a storage device may store one or more power loss thresholds for comparison to the calculated values for Heat_CO such that if Heat_CO exceeds the threshold in use at the time, the system may reduce the power level with which primary coil 76 is being driven, in turn reduce power transmitted to IMD 2 and object 8, and reduce heat dissipation for these elements.

Similar threshold values as discussed above with respect to object 8 may be stored in conjunction with heat dissipated by primary coil 76 and IMD 2. As was the case with power loss thresholds associated with the object 8, such thresholds may be determined using modeling techniques that take into account such things as the size, shape, location, and material used to construct the primary coil 76 and IMD 2. The location within the body of the IMD 2 (including relative location to object 8), patient preferences, and other factors may contribute to the selected thresholds.

In one embodiment, the heat thresholds selected for both primary coil 76 and IMD 2 may each be selected such that heat dissipated by primary coil 76 will not cause the coil to have a temperature increase above some predetermined temperature (e.g., 43 degrees C.). Similarly, the heat threshold for IMD 2 may be selected so the temperature rise of the can of IMD 2 will not rise above the same, or a different predetermined temperature. These heat thresholds can be determined empirically or using known modeling techniques.

As was the case with the thresholds associated with object 8, thresholds for heat dissipation associated with IMD 2 and primary coil 76 may be programmably selected or selected by a manufacturer (e.g., "hardcoded"). When the thresholds are selectable, a user such as a patient, clinician, or other user may be allowed to make the selection in some examples. In some cases, more than one threshold may be available for selection within the system, such as for use by patients that are either more, or less, tolerant to heating during recharging. In some cases, the user may be allowed to enter their own threshold, so long as the threshold falls within limits as determined by safety constraints and/or manufacturer specifications.

In accordance with the foregoing, respective threshold values may be associated with heating of IMD 2, object 8, and/or the primary coil 76 (i.e., Heat_IMD, Heat_CO, and Heat_Primary, respectively). These thresholds may be stored in any one or more of the storage devices available within the system. In one example, system 48 may conduct recharge such that none of the thresholds are exceeded. If a threshold is being exceeded, system 48 may reduce the amount of power being delivered to primary coil 76, as by reducing the duty cycle at which the H-bridge circuit is being driven, until the limiting one of the thresholds is no longer being exceeded.

As an example, in one embodiment, the amount of power lost to heat in an IMD is limited to 600 mWatts. This IMD is implanted in a vicinity of an artificial hip that is known to be capable of absorbing a relatively large amount of power without exceeding regulatory limits associated with temperature increases, and therefore the threshold for power lost to heat is set to 1200 mWatts for this object 8. During recharge, system 48 controls power delivery to primary coil 76 such that neither threshold is exceeded. While in this case, the limiting factor is likely the heat absorption of the implant, in other cases involving smaller object 8 capable of absorbing less power, the limiting threshold may be associated with the object 8 rather than IMD 2. In still other cases, the limiting threshold may be associated with the primary coil.

In some cases, recharge may be controlled based not only on the amount of power being dissipated but also on one or more temperature limits. For instance, a temperature limit may be associated with primary coil 76. If the temperature of primary coil 76 exceeds this temperature limit, as may be determined by one or more temperature sensors, such as temperature sensor 95, recharge system 48 may reduce the power delivered to primary coil 76. Similarly, one or more temperature sensors within IMD 2 may be used to record temperature at various locations within IMD 2. These temperature measurements may be transferred via telemetry to recharge system 48. If any of the temperature readings exceed one or more temperature thresholds established for IMD 2, recharge system 48 may reduce power delivery to primary coil. Thus, while heating dissipation limits may be used to limit power lost to heating for a given element within the system, temperature limits may be associated with such elements as well.

In other examples, power may likewise be controlled based on a maximum allowable current level flowing to power source 50 during recharge. Thus, even if heat thresholds are not exceeded, it may be desirable to throttle power delivered by primary coil 76 based on a recharge current exceeding a maximum allowable current.

Thus, in the foregoing manner, multiple power loss thresholds and/or other thresholds, may be used alone or in conjunction with one or more temperature thresholds, may be used to control power delivered to primary coil 76 (and resulting power delivery by primary coil 76 to IMD 2 and object 8) for recharging a rechargeable power source 50 of IMD 2.

Some or all of the processing steps used to determine whether the thresholds are exceeded may be performed by control circuit 88 of charging circuit 70 and/or control circuit 52 of IMD 2. For instance, values such as Power_Charge and Heat_IMD may be determined by control circuit 52 of IMD and transmitted to control circuit 88, which may then determine values for Heat_IMD and Heat_CO. In another embodiment, at least some of the processing steps may be performed by control circuit 71 of external device 100 that is connected to charging circuit 70 via interface 84*a*. For instance, external device 100 may communicate via telemetry circuit 69 with IMD 2 during recharge to receive information including, but not limited to, a current and voltage of power source 50, and temperature at one or more locations within IMD 2.

External device 100 may further receive current, voltage, and other parameters associated with the driving of the H-bridge circuit so that values for Power_Primary and Heat_Primary may be determined. External device 100 may thereby determine whether any of the power loss values, including Heat_Primary, Heat_IMD, or Heat_CO has exceeded acceptable limits. If so, external device 100 may provide an indication to charging circuit 70 to decrease the power level in the primary coil 76 by some determined amount. Alternatively, external device may provide the specific adjustments to charging circuit 70 (e.g., decrease duty cycle by some specified amount, etc.) In this manner, external device 100 may perform at least some of the processing steps used to control power being delivered to primary coil 76, thereby off-loading at least some tasks from charging circuit 70. Thus, it may be understood that processing steps may be performed by various combinations of control circuit 71, control circuit 88 and control circuit 52.

As examples of a power level at which primary coil 76 may be driven during recharge (i.e., Power_Primary), a relatively high power level may be approximately 2.5 Watts whereas a lower power level may be approximately 1.0 milliwatts (mW). An example charge current level achieved flowing to power source 50 during recharge may be approximately 100 milliamps (mA) for a high power level in the primary coil. The recharge current may be approximately 60 mA for a low power level in primary coil 76. An example primary coil voltage and current for a high power may be approximately 450 V and approximately 800 mA, respectively, and an example primary coil voltage and current for a low power level may be approximately 250 V and approximately 500 mA. These values are merely examples, and other examples may include higher or lower values in accordance with the current disclosure.

As previously discussed, when it is determined that a power loss threshold has been exceeded, there are several ways to adjust the power in primary coil 76. In particular, charging circuit 70 may alter voltage at node 154 and/or the duty cycle of the drive signal. In one example, Power_Primary is more sensitive to a change in duty cycle than a change in voltage. Thus, when a power change is needed, control circuit 88 may first adjust the duty cycle. In one embodiment, the adjustment will be limited such that the final duty cycle is within low and high limits. In one embodiment, the pulse of a pulse train driving either of switches 150 and 156 must be between 1000 ns and 6000 ns. This is between about 4% and 26% for the signal driving switch 150 or 156, or double these values if both switches 150, 156 are taken into account. Other duty cycle limits can be used in the alternative, keeping in mind that for a single one of switches 150 or 156, the duty cycle must be something less than 50% to take into account the dead period. If the degree of power adjustment that is needed cannot be achieved by adjusting the duty cycle within these limits, control circuit may then further adjust voltage at node 154.

In one example, after charging circuit 70 either determines a level by which power may be adjusted, or alternatively receives the level of adjustment from external device 100, charging circuit 70 may utilize one or more look-up tables (e.g., as may be stored within storage device 90) to determine how to achieve this adjustment. In one example, the presently-used frequency of the drive signal and the amount of the adjustment that is required may be provided as input to the look-up table to determine an amount by which to alter duty cycle and/or voltage at node 154. Such an embodiment may assume that the voltage and current in the primary coil 76 are in phase with one another. In another case, information concerning the phase difference between these two signals, as may be determined in a manner described above, may be provided as an additional input to the lookup table(s). In still another example, storage device 90 may store one or more equations instead of lookup tables (such as the power equations described above) to determine the changes needed to the duty cycle and/or H-bridge voltage. Such equations may be based on modeling of the circuit driving primary coil 76 (e.g., H-bridge circuit.) For instance, the equations described above may be used to determine how much adjustment in duty cycle and/or voltage is required to achieve a particular adjustment to Power_Primary and Heat_Primary.

Adjustment of the power level provided to primary coil 76 (Power_Primary) may be performed at various time intervals. In one example, the frequency at which primary coil 76 is driven by control circuit 88 is adjusted periodically to maintain the signal at the resonant frequency of the system, which is affected by such things as positioning and flexing of antenna 78. Tuning of power may occur whenever this frequency tuning occurs. In another example, tuning of the power in the primary coil 76 may be performed more often than tuning of the frequency. For instance, it may be performed at predetermined time increments, such as an increment of between 30 seconds and 5 minutes. In one example, it may be performed every minute.

In one example, Power_Primary is maintained at a level such that the limiting one of Heat_Primary, Heat_IMD, and Heat_CO is just under desired limits. This will allow energy transfer to complete as quickly as possible. Thus, after determining values for Heat_Primary, Heat_IMD, and Heat_CO in any of the aforementioned ways, and if all of these values are below acceptable limits, it may be desirable to increase Power_Primary so that the limiting one of these values will be increased to just below limits.

Figure 4A:
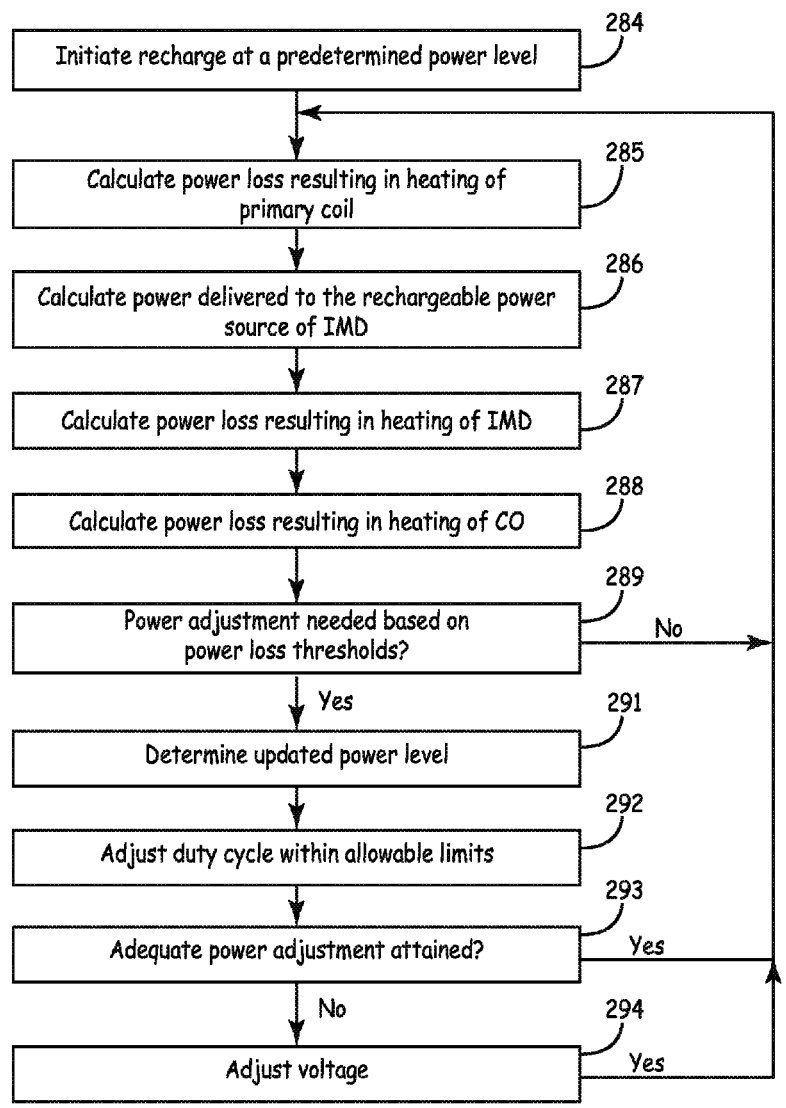
FIG. 4A is a flow diagram of a method of controlling transcutaneous transfer of energy in the presence of object 8.

FIG. 4A is a flow diagram of adjusting power in the primary coil according to one example method. First, recharge may be initiated at a predetermined power level (284). In one embodiment, the power level selected for this purpose is the power level needed to obtain a predetermined recharge current that is being provided to rechargeable power source 50 of IMD 2 for the given implant scenario. This current may be measured by IMD 2 and communicated telemetrically to charging circuit 70. To achieve this predetermined recharge current, the duty cycle of the H-bridge drive signal and/or voltage of the H-bridge circuit may be adjusted appropriately. In one example, the frequency of the drive signal may be selected to be the resonant frequency of a system, including object 8.

Next, power loss resulting in heating of the primary coil may be determined (285). In one instance, this is determined as the product of the square of the RMS current through the primary coil 76 and the AC series resistance of primary coil 76. The RMS current may be measured in one embodiment and the AC series resistance of the coil is a known value that depends on the design of the coil and which may also be determined empirically, as discussed above. This value may also be determined using known circuit modeling techniques.

The power delivered to the rechargeable power source of IMD 2 may also be determined (286). In one embodiment, this is determined as the product of the voltage of rechargeable power source 50 and the current being delivered to this power source. Both of these values may be measured by circuitry within IMD 2 and provided via telemetry to charging circuit 70 and/or to external device 100. In some cases, voltage of power source 50 may not vary substantially during recharge, in which case merely determining the recharge current being delivered to the power source can be used as a surrogate metric for power delivered to the power source.

The power loss associated with heating of IMD 2 (i.e., Heat_IMD) may be determined (287). As discussed above, this value may be calculated in various ways, including using design constants coupled with measuring various currents within the IMD during recharge. Alternatively or additionally, this value may have been previously determined (e.g., using Equation 1 and measured values for Power_Charge that were obtained when energy was being transferred to IMD in the absence of object 8 while substantially the same recharge and implant scenario existed.) Yet another variation may employ one or more temperature measurements as a surrogate for the power measurements to determine Heat_IMD.

The power loss resulting in heating of object 8, Heat_CO, may also be determined (288). This determination may be made by subtracting Heat_Primary, Power_Charge, and Heat_IMD from Power_Primary.

It may also be determined whether a power adjustment is needed based on the power being dissipated by any of the primary coil 76, IMD 2, or object 8 (289). Specifically, each of Heat_Primary, Heat_IMD, and Heat_CO may be compared to a respective power threshold. In one example, if a determined heat value exceeds a respective threshold, power delivered to the primary coil 76 is reduced.

It may be desirable in some instances to impose a limit on cumulative heating. For instance, if IMD 2 and object 8 are determined to be in close proximity to one another, it may be desirable to take into account the total heat dissipation associated with IMD 2 and object 8. For instance, even though heating associated with IMD 2 and object 8 are both below associated individual thresholds, if IMD 2 and object 8 are in close proximity to one another, the total amount of heat dissipation to a relatively small area of tissue may be above what is considered comfortable and safe for the patient. In this type of scenario, another cumulative threshold may be defined to limit the cumulate heating represented by Heat_IMD+Heat_CO. In still another example, another threshold associated with Heat_IMD+Heat_CO+Heat_Primary may be used to limit all heating within the system. Such cumulative thresholds may take into account one or more factors such as distance and relative orientation between object 8 and IMD 2, depth of implant, a type of tissue surrounding IMD 2 and object 8, and so on.

In one example, if heat dissipation for primary coil 76, IMD 2 and object 8 are all below their respective limits, and any cumulative heat dissipation threshold in use in the system is not exceeded, it may be desirable to increase the power level so that recharge completes more quickly. In this case, it may be desirable to adjust the power level in the primary coil 76 in attempt to maintain the limiting one of Heat_Primary, Heat_IMD, and Heat_CO right at the threshold level so that recharge completes as fast as possible without exceeding limits.

If an adjustment is deemed to be needed in step 289, a new power level with which to drive primary coil 76 (i.e., Power_Primary) may be determined based on an amount by which the limiting one Heat_IMD, Heat_CO or Heat_Primary is above or below the target value (291). The amount by which the power level is adjusted may be proportional to how far away the heat dissipation value or other limit is from the target value. In another embodiment, the amount of the adjustment may be some incremental predetermined amount that is applied regardless of how far away an actual value is from the respective target. In any event, the updated power level resulting from the adjustment may be saved for use as Power_Primary in the power loss calculations.

Optionally, step 289 of determining a new power level may also take into consideration a deviation of another limiting factor (e.g., a temperature measurement) from a target threshold value. For instance, a temperature of the primary coil 76 may be obtained via temperature sensor 95. One or more additional temperature measurements may be taken at various locations within IMD 2 or at another location of the patient's body via one or more temperature sensors 51. These temperature measurements may be compared to respective temperature thresholds to determine whether any temperature thresholds have been exceeded. If any of these additional threshold limits are exceeded, power may be adjusted accordingly.

As another example of a limiting factor, a limit may be placed on the recharge current flowing to power source 50. For instance, if this current is exceeding some predetermined maximum recharge current value, power may be reduced. This maximum current value may be a hard system limit that applies to all recharge and implant scenarios, or may be selected based on the current recharge and implant scenario. For instance, this current value may be a value associated with an angled implant scenario and a predetermined implant depth or may be a "hard" limit based on a type of power source 50.

In the foregoing manner, in some examples, even if a power limit is not being exceeded, power may still be adjusted based on an additional limit check. Such additional limits may provide safeguards that supplement the use of the power limits.

Next, the adjustment to the power level may be used to determine new drive parameters for driving the H-Bridge circuit. As previously discussed, this may involve adjusting the H-bridge duty cycle (292). In one embodiment, this adjustment is made within predetermined allowable limits. For instance, the duty cycle for one switch pair cannot exceed about 26% although other values may be used in the alternative. It may further be desirable to set a lower limit such as about 4% for the duty cycle of one switch pair of the H-bridge circuit. Any limits may be selected for this purpose so long as the duty cycle for one switch pair is somewhat less than 50% to accommodate the dead period discussed above.

In one example, the amount and manner by which the limiting one of the heat dissipation values deviates from a respective threshold may instead be used to reference one or more lookup tables to determine an amount to vary the duty cycle. For instance, an amount by which Heat_CO exceeds the corresponding threshold currently in use by the system is employed to reference one or more lookup tables to determine an amount to vary the duty cycle. This determination may take into account the duty cycle, the frequency and/or the voltage at which node 154 is being presently being driven. In another example, instead of lookup tables, equations such as Equation 2 above and the relationship between current, voltage, and phase angle of the primary coil may be used to determine an amount by which to alter the duty cycle.

If the entire power adjustment that is required cannot be achieved solely through a duty cycle adjustment (293), the voltage level of the H-bridge circuit may be adjusted to bring the power level of primary coil 76 to the desired value (294). Again, the portion of the power adjustment that could not be accomplished through duty cycle modification may be mapped to a voltage adjustment by using one or more lookup tables. Alternatively, equations such as those discussed above may be used for this purpose. Processing may then return to step 285 to repeat the process.

While the foregoing approach uses a duty cycle adjustment as the primary means for controlling power in primary coil 76, in another example, a power adjustment may be made by first adjusting voltage of the H-bridge circuit. Only if this is not sufficient will duty cycle then be adjusted. In another embodiment, a given adjustment is made by changing both duty cycle and voltage to achieve a given power adjustment.

In an alternative embodiment that utilizes a signal generator rather than an H-bridge circuit, an input to the signal generator may be modified to alter a characteristic of the signal provided to primary coil 76 and thereby modify the power level transmitted to IMD 2 and object 8. Such a characteristic may involve the shape, duty cycle, frequency, amplitude, pulse width, and so on, of the waveform generated by the signal generator. As was the case above, the specific adjustment can be obtained by using the size of the power adjustment to reference one or more lookup tables.

Power adjustment in primary coil 76 may be performed repeatedly throughout a recharge session, as shown in FIG. 4A. Alternatively, steps of FIG. 4A may be performed at regular intervals (e.g., intervals ranging from 30 seconds to 5 minutes). In one specific embodiment, this occurs every minute. In yet another example, execution of the process may be performed upon occurrence of a trigger event. For instance, when telemetry communication from IMD 2 indicates a significant change has occurred to the power being delivered to rechargeable power source 50, indicating possible change in relative positioning between the primary and secondary coils, the process of FIG. 4A may be performed to adjust power to primary coil 76 if such an adjustment is needed.

As previously discussed, various steps of FIG. 4A may be performed by control circuit 52, control circuit 88, and/or control circuit 71. In one example, at least some of the processing steps may be off-loaded to external device 100. These steps may be performed using hardware circuitry, programmed instructions, or any combination thereof. Some, or all, of the steps of FIG. 4A may be performed automatically without prompting from a user.

It will be appreciated that the method of FIG. 4A is merely an example. In some scenarios, only a single threshold need be checked such that some steps may be omitted. For instance, it may be known that in all cases, the threshold associated with heating of object 8 will be the limiting factor associated with power delivery during recharge. In this case, checking heating for IMD 2 and primary coil 76 may not be needed and these steps may be eliminated. In another case, it may be determined that no checking of temperature thresholds is needed because it is known that so long as the one or more heat thresholds are considered, temperature limits will remain within acceptable ranges.

In still other embodiments, one or more of the duty cycle or voltage adjustment steps and corresponding checks may be omitted because it is known that adjustment of one of the duty cycle or voltage will always be adequate to achieve acceptable results. In another embodiment, some other adjustment may be made, such as adjusting the shape, duty cycle, amplitude, period, and/or frequency of a continuous waveform that is being generated by a signal generator for driving primary coil. Additionally, in some cases, the ordering of the steps in FIG. 4A may be changed. Thus, FIG. 4A is illustrative in nature and not limiting.

FIG. 4A contemplates calculation or estimation of a value for Heat_IMD, which describes heating of the IMD. This value may, in turn, be used to determine the value for Heat_CO when IMD 2 is in the presence of a conductive object 8. In other examples, simplifications may be performed so that estimation of this value is not necessary.

As one example of a simplification of FIG. 4A, when IMD 2 is not in the presence of object 8, several power measurements may be made. Such measurement may be made, for instance, when IMD 2 is implanted within the patient before object 8 is present in, or on, the patient's body. Alternatively, these measurement may be made by placing IMD 2 in a controlled environment similar to an implant environment (e.g., in a gel bath) in the absence of object 8 while energy is being transferred to the IMD using a configuration similar to that which will be used when IMD 2 is implanted in a body.

In either case, measurements may be made to determine how much power must be delivered by the primary coil 76 to IMD 2 to achieve a predetermined recharge current flowing to power source 50 of IMD 2. Assuming the recharge voltage is relatively constant, this recharge current will be associated with some predetermined recharge power level (Power_Charge). Alternatively, the voltage may be measured to determine Power_Charge. In either case, a reference value for Power_Primary−Heat_Primary may be determined using techniques described above that will be associated with this value for Power_Charge. If desired, this value may be determined at various intervals throughout one or more recharge sessions, with an average for Power_Primary−Heat_Primary being determined and stored as a reference for later use. As may be appreciated from the foregoing equations and discussion, a predetermined value for Heat_IMD will be associated with the level of Power_Charge, although this specific value need not be explicitly determined, if desired.

At a later time, when IMD 2 is known or suspected to be in the presence of object 8, a new value for Power_Primary−Heat_Primary may be determined that is required to achieve the same predetermined recharge current to power source 50. It may be assumed that at this predetermined recharge current and for a particular implant scenario, a same value for Heat_IMD will exist within the system as existed at the time of the previous measurements. As such, it can be assumed that any additional heat associated with Power_Primary−Heat_Primary is being absorbed by the conductive object 8. Power delivery to the primary coil 76 may be controlled by the amount the current value for Power_Primary−Heat_Primary exceeds the previously-stored reference value. In this manner, the determination as to how to control power delivery may be simplified somewhat, since a value for Heat_IMD need not be calculated or estimated to estimate heat loss associated with the object.

Figure 4B:
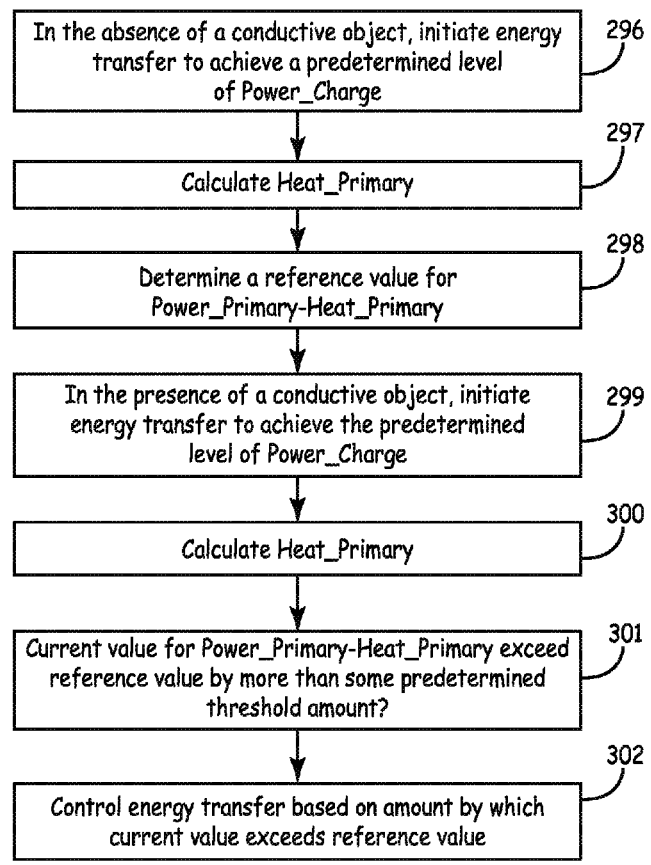
FIG. 4B is flow diagram of another method of controlling transcutaneous transfer of energy in the presence of object 8.

FIG. 4B is an example method of controlling the transcutaneous energy transfer without the need to determine values for Heat_IMD or Heat_CO. In one embodiment, energy transfer may first be performed in the known absence of object 8 at a power level needed to achieve a predetermined level of power delivery to power source 50 (296). As previously discussed, the amount of power delivered to power source 50 may be determined as the product of the voltage of rechargeable power source 50 and the current being delivered to this power source. Both of these values may be measured by circuitry within IMD 2 and provided via telemetry to charging circuit 70 and/or to external device 100. Assuming voltage during recharge is relatively constant, it may only be necessary to determine that a predetermined recharge current has been achieved.

During this reference recharge session, power loss resulting in heating of the primary coil may be determined (297). In one instance, this is determined as the product of the square of the RMS current through the primary coil 76 and the known AC series resistance of the coil, which is a constant that can be determined empirically or derived based on the coil design.

One or more values for Power_Primary−Heat_Primary may be determined over one or more recharge sessions. If desired, one of these values or some combination of the values (e.g., an average) may be used as a reference value for Power_Primary−Heat_Primary (298).

At a later time when IMD is known or suspected to reside in the presence of object 8, the amount the power needed to achieve a predetermined level of power delivery to power source 50 may again be determined (299). Also, the power loss resulting in heating of the primary coil may also be determined (300). It may be determined whether the currently-determined value for Power_Primary−Heat_Primary exceeds the previously-stored value for Power_Primary−Heat_Primary by more than some predetermined threshold amount (301). Assuming a same recharge and implant scenario as existed when the reference recharge session was conducted in the known absence of object 8, it may be concluded that this additional amount of power that exceeds the reference power value determined in step 298 is being dissipated as heat in object 8.

If it is determined in step 301 that Power_Primary−Heat_Primary exceeds some threshold value such that energy transfer is to be controlled, the power level may be adjusted appropriately (302). This may be accomplished using techniques such as those described above in regards to FIG. 4A. For instance, look-up tables may be used to map adjustments to H-Bridge duty cycle and/or voltage to an amount by which the current value of Power_Primary−Heat_Primary exceeds the saved reference value.

The simplified method of FIG. 4B may be performed to determine when power delivery is to be throttled. Some, or all, of the steps of FIG. 4B may be performed automatically using one or more of the control circuits included in the system. Using this simplified method, there is no need to explicitly calculate values for Heat_IMD and Heat_CO during each recharge session, saving processing steps.

As may be appreciated, the reference value for Power_Primary−Heat_Primary as determined in step 298 may be determined post-implant when IMD 2 is in the known absence of object 8. Alternatively, the reference value may be determined by placing IMD 2 in a gel bath or other controlled environment that simulates a particular implant scenario. For instance, IMD 2 may be placed in a gel bath according to a given implant scenario, including implant depth and relative orientation between the primary and secondary coils. A level for Power_Primary−Heat_Primary that will result in a predetermined value for Power_Charge may then be determined. This information, including information associated with the recharge and implant scenario, may be stored for later use post-implant when the IMD is implanted in the presence of object 8. Multiple associations may be recorded for various implant and recharge scenarios (e.g., various levels of Power_Charge, implant depth, coil orientation, etc.)

After IMD 2 is implanted, a given lookup table may be selected for use with a then-current implant scenario and a desired recharge scenario. An appropriate table may be selected once after implant or alternatively before each recharge session. Power may then be delivered from the primary coil to achieve the previously-recorded level of Power_Charge. The amount of power delivered to achieve this (i.e., Power_Primary−Heat_Primary) is determined so that heat attributable to object 8 may be determined in the aforementioned manner. Thus, using a gel bath to develop one or more tables or other data structures allows a method such as shown in FIG. 4B to be used when object 8 is implanted or otherwise is presence prior to implant of IMD 2.

Another technique for controlling power delivery to prevent overheating of object 8 involves performing a frequency sweep to obtain a "loading profile" over a range of frequencies that may surround the resonant system frequency. Such a loading profile indicates how power associated with a given element of a system (e.g., power being provided to IMD 2) varies as a function of frequency. The loading profile provides an indication of how heating varies over the range of frequencies. This is described further in reference to FIG. 5.

Figure 5:
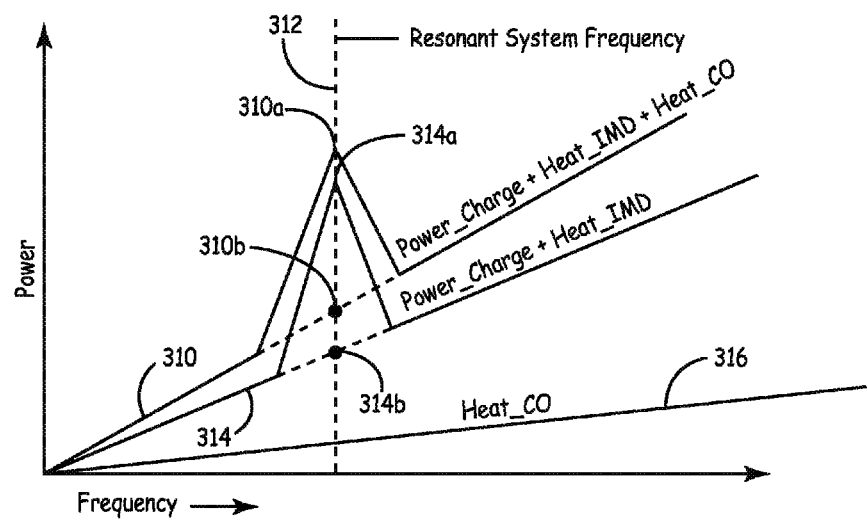
FIG. 5 is an example waveform diagram of loading profiles obtained when transcutaneously transferring energy to an IMD over a range of frequencies.

FIG. 5 is an example waveform diagram illustrating use of a loading profile. To obtain this loading profile, control circuit 88 varies a frequency at which tank circuit 165 is driven to transfer energy to IMD 2 and object 8. The frequency at which tank circuit 165 is driven varies along the X axis whereas power provided into various loads is shown along the Y axis. Waveform 310 illustrates total power provided by the primary coil 76 to an IMD and object 8 across various frequencies. Waveform 314 illustrates total power provided by primary coil 76 to the IMD alone when object 8 is not present across various frequencies. Both waveforms exhibit a peak at a resonant system frequency 312 (shown dashed). At this frequency, the quality of inductive coupling between primary coil 76 and secondary coil 56 is at a maximum and the amount of energy that can be supplied to rechargeable power source 50 over a given amount of time is therefore also at a maximum.

Waveform 314 may be measured by positioning IMD 2 within a controlled environment that models a typical implant scenario in a human body without the inclusion of object 8. For instance, IMD 2 may be implanted in a patient who has not yet been implanted with any other objects. Alternatively, IMD 2 may be placed in a gel bath that models implantation of the device in a human body without the presence of object 8. In either case, antenna 78 may be positioned at a location from secondary coil 56 that corresponds to a typical recharge scenario, with this positioning achieving at least adequate coupling between the two coils, and hence adequate recharge current flowing to power source 50 in one embodiment.

While the location of antenna 78 remains stationary at the predetermined acceptable location for recharge, control circuit 88 (FIG. 3) may vary the frequency at which switch pairs 150, 152 and 156, 158 of the H-bridge circuit are driven. Control circuit 88 may start the sweep below the resonant frequency of the system, progressively increasing frequency until the tank circuit 165 is being driven at a frequency above resonant frequency of the system. Alternatively, control circuit 88 may begin the sweep above the system resonant frequency, progressively decreasing frequency to a frequency below the resonant frequency of the system.

During the sweep of the frequency, control circuit 88 may monitor a signal from voltage detector 232 and provide feedback to power conversion circuit 74 so that power conversion circuit maintains the voltage at node 154 substantially constant throughout the frequency sweep. Moreover, the duty cycle will likewise by maintained at substantially a constant level during the frequency sweep. Assuming the location of antenna 78 remains the same and the voltage level and duty cycle used to drive the tank circuit 165 are likewise held constant, the current through the tank circuit will be at a maximum at the resonant system frequency in the manner shown by peak 310*a*.

The RMS current and RMS voltage can be determined for the tank circuit 165 in the manner described above. Moreover, the angle between tank voltage and current may be monitored during the frequency sweep (e.g., using detect circuit 160, which determines zero crossings of the two signals.) A discussed previously, assuming both the voltage and current in primary coil 76 are sine waves, the amount of power delivered to the primary coil, Power_Primary, is the product of the RMS current in the primary coil, the RMS voltage across the primary coil, and the cosine of the phase angle between these two signals. Values for Power_Primary can thus be determined at various frequencies during the frequency sweep for the particular implant scenario that is being modeled (e.g., based on the separation and angles of the coils, etc.).

During recharge, some power is dissipated as heat in the primary coil as is previously discussed. This dissipated power, Heat_Primary, is the product of the square of the RMS current in the primary coil determined in the manner discussed above, and a known system constant value for the AC series resistance of primary coil 76 at the nominal resonant frequency.

It may be noted that the AC series resistance of primary coil 76 may vary as frequency varies such that use of a single constant value for this coil resistance may not, in some examples, be accurate throughout the frequency sweep. As such, in one embodiment, the AC series resistance of the primary coil 76 may be determined at various frequencies to be used in the frequency sweep. These values may be determined either empirically using the mechanism discussed above or using modeling techniques.

Once frequency-dependent AC series resistant values have been determined, an appropriate resistance value for a given frequency may be selected for use in determining a more accurate value for Heat_Primary at that frequency. These frequency-dependent values for Heat_Primary may then be subtracted from a corresponding value for Power_Primary to obtain waveform 314. This waveform represents all of the power delivered by the primary coil to the IMD in the absence of object 8. This power will either be used to charge rechargeable power source 50 (i.e., Power_Charge) or will result in heating of the IMD (i.e., Heat_IMD).

In an alternative embodiment, instead of using various values for the AC series resistance of the primary coil to obtain data for waveform 314, it may be sufficient to use the AC series resistance value that corresponds to system resonant frequency throughout the frequency sweep as a "good enough" approximation. This approximation may be considered "good enough" because, in one embodiment, it is the data around the system resonant frequency that is considered most important, and the values for Heat_Primary around this frequency will be substantially accurate.

It may be noted that waveform 314 may likewise be obtained by control circuit 88 varying the frequency of the tank circuit 165 while measurements are taken within IMD 2 to obtain values used to calculate Power_Charge and Heat_IMD. These two calculated values may then be added together and plotted against frequency to obtain waveform 314. Techniques for measuring or otherwise determining values for Power_Charge and Heat_IMD are discussed above. Further, if desired, individual waveforms for one or both of Power_Charge and Heat_IMD may be plotted against frequency using the individual calculated values.

Regardless of how waveform 314 is generated, values for Power_Charge may be stored along with waveform 314 for various frequencies included in the frequency sweep.

Any or all of the above-described waveforms may be derived in a controlled environment (e.g., prior to implant or after implant and in the absence of object 8) and stored within a storage device of the IMD 2, charging circuit 48, and/or external device 100 for later use after implant, if desired.

After IMD 2 has been implanted and is in proximity to object 8, and assuming a typical recharge scenario of a type that was modeled when waveform 314 was obtained (e.g., similar orientation and spacing of primary coil with respect to the secondary coil), another frequency sweep may be conducted. At each frequency, primary coil 76 will be driven at a power level that will achieve substantially a same value for Power_Charge as was achieved at this frequency when waveform 314 was generated. This will result in substantially similar Power_Charge and Heat_IMD values at this frequency as existed during the prior frequency sweep.

During this frequency sweep, similar steps as described above may be performed to determine Power_Primary and Heat_Primary. When values for Heat_Primary are subtracted from Power_Primary, waveform 310 is obtained. This waveform reflects not only Power_Charge and Heat_IMD, but also represents the power lost to heating of object 8, Heat_CO. By subtracting waveform 314 from waveform 310, waveform 316 is obtained that represents heating of object 8.

The frequency sweep mechanism illustrated by FIG. 5 may be somewhat processing intensive, since the frequency sweep must be performed to obtain waveforms such as waveform 310 and 314. However, these waveforms can yield important information that is not readily available with some other methods. For example, in considering waveform 314, a peak-to-baseline ratio may be derived that compares the power level at point 314*a* to a baseline power level corresponding to point 314*b*, wherein the baseline power level is the value obtained by interpolating the portions of the curve that are not associated with resonant frequency (e.g., according to dashed portion of curve on which point 314*b* lies) to yield a power level that would be associated with the system if frequency 312 were not associated with resonance. In other words, the baseline power level is a power level that would be associated with the system at that frequency if this frequency were not a resonant frequency of the system. The peak-to-baseline ratio may be determined from waveform 314 and stored within a storage device of IMD 2, charging system 48, or external device 100 for later use.

Next, consider a similar peak-to-baseline ratio derived from waveform 310. Again, this is the ratio of the peak power level at point 310*a* to the baseline power level at point 310*b*. If object 8 is present, this ratio will be smaller than the peak-to-baseline ratio for curve 314 and/or the peak may shift to a different frequency than is obtained for the peak of waveform 314. Specifically, in this example, the ratio between the power level represented by point 310*a* and that represented by point 310*b* will be smaller than the ratio between the power level represented by point 314*a* and that represented by point 314*b*. The power loss within object 8 may be proportional to the amount of this ratio reduction. Thus, by performing a very limited scan around the known system resonant frequency, it can very quickly be determined whether object 8 is absorbing power during the transfer of energy to IMD 2 at a predetermined frequency. If a sufficient amount of power is being absorbed, it may be necessary to control energy transfer as previously discussed.

The amount by which the peak-to-baseline ratio is smaller in the presence of object 8 than the ratio obtained in the absence of object 8 may be directly correlated to the value for Heat_CO. For instance, such a correlation may be performed once by driving tank circuit 165 at different power levels, determining the amount of ratio reduction at each of these power levels, and correlating the amount of ratio reduction with corresponding values for Heat_CO, as may be determined using techniques described herein (e.g., in relation to Equation 1.)

As discussed above, the values for Heat_CO that are considered acceptable may be based on a number of characteristics of object 8, including a shape, material construction, size, texture of a surface that contacts tissue, location within the body, and so on. An amount of heating for a given object can be determined by modeling, with acceptable heat threshold limits being based, in one example, on a temperature rise associated with the heat dissipation. Thus, values for thresholds associated with Heat_CO are specific to a given implant scenario and may be determined by measurements (e.g., when object 8 is in a controlled environment prior to implant, for instance) and/or using modeling techniques. These values may also be user-selectable to accommodate user preferences.

In the foregoing manner, the amount by which the peak-to-baseline ratio is smaller than it would otherwise be in the absence of object 8 may be mapped to an Heat_CO value, and this Heat_CO value may be compared to a threshold to determine what type of adjustments need to be made by control circuit 88 in driving tank circuit 165. Such adjustments may involve adjustments to duty cycle and/or voltage, as discussed in reference to FIGS. 4A and 4B. As further described in reference to these figures, in some examples, an amount by which Heat_CO exceeds a threshold may be mapped to an amount of a duty cycle and/or voltage adjustment (e.g., via lookup tables, for instance) so that control circuit 88 may readily determine using the lookup tables how to adjust the driving of tank circuit 165 in a given circumstance. Such tables may also take into account a frequency, duty cycle, and/or voltage at which the tank circuit is presently being driven. In another example, equations such as those discussed above may be used to derive the adjustments to be made to the tank circuit.

In one embodiment, an amount by which the peak-to-baseline ratio is smaller than it would otherwise be in the absence of object 8 may be mapped directly to the adjustment needed in the driving of the tank circuit. This may eliminate the intermediate step of first converting the change in the ratio to a value for Heat_CO, and then translating the value for Heat_CO into a change in the way tank circuit 165 is being driven. Thus, it may be appreciated that the change in peak-to-baseline ratio may be used in a manner similar to the way the determined heat values are used in FIG. 4A and the way the change in Power_Primary–Heat_Primary is used in FIG. 4B to adjust power.

Figure 6:
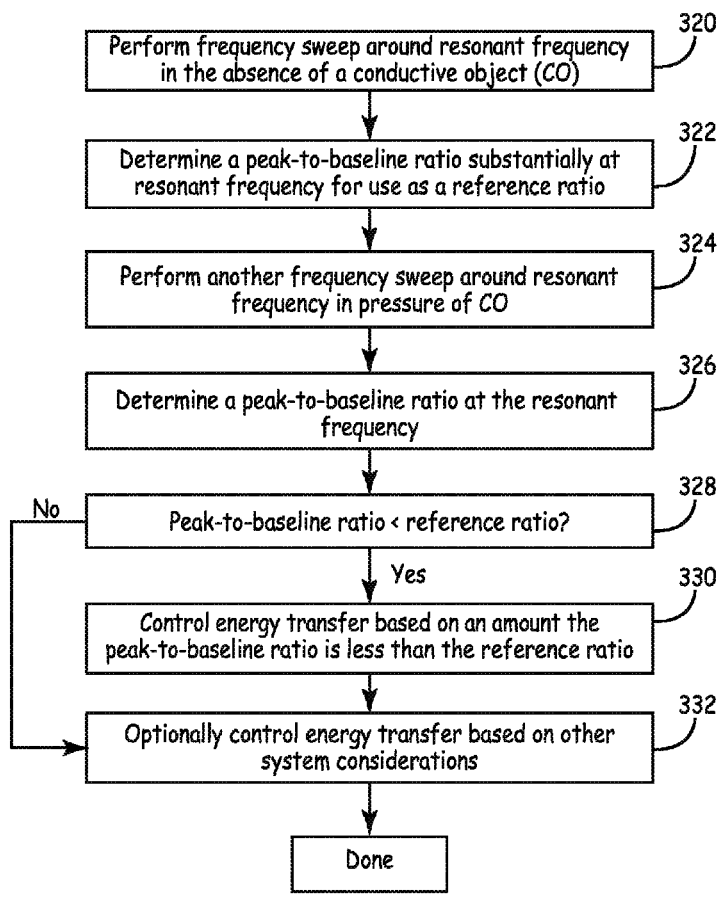
FIG. 6 is an example method of controlling transcutaneous transfer of energy based on peak-to-baseline ratios.

FIG. 6 is an example method of using peak-to-baseline ratios in controlling power delivery in the presence of object 8. A frequency sweep may be performed by control circuit 88 in driving tank circuit. This scan may be performed around the resonant frequency of the system that includes system 48 and IMD 2 (320). This scan will produce a waveform from which a peak-to-baseline ratio may be determined (322). This peak-to-baseline ratio may be derived at substantially the resonant system frequency. This is the ratio between the power being provided from primary coil 76 to IMD 2 at the resonant frequency as compared to the baseline power value obtained if there were no resonance at this frequency. The baseline value may be obtained by extrapolating the waveform portions that are not associated with the resonant frequency in some instances. This ratio may be saved as a reference ratio for future use in determining heating to be attributed to object 8. Further, at various frequencies during the sweep, values for Power_Charge (e.g., as may be indicated by the recharge current assuming voltage for power source 50 remains constant).

At a time when object 8 may be, or is suspected to be, present, another frequency sweep may be performed that includes the resonant frequency (324). At a given frequency, primary coil 76 is driven to obtain substantially the same Power_Charge to power source 50 (e.g., as may be determined based on obtaining the same recharge current to power source 50.) This sweep will be used to derive a power waveform similar to waveform 310 of FIG. 5 using techniques previously described. From the sweep data, another peak-to-baseline ratio may be obtained (326). It may be determined whether this ratio is less than the reference ratio (328). If not, control over power delivery may continue without presently taking into account the heating of object 8, but instead optionally taking into account other system considerations (332). For instance, assuming the new peak-to-baseline ratio is not smaller than the reference ratio, power delivery may occur based on whether heating associated with primary coil 76 or IMD 2 is a limiting factor in the power delivery, or whether temperature rises have exceeded predetermined limits. In some cases, the additional factor may be the recharge current flowing to power source 50 which is compared to a maximum allowance recharge value.

If the peak-to-baseline ratio is less than the reference ratio (328), the transfer of energy may be controlled based on an amount the peak-to-baseline ratio is less than the predetermined ratio (330). In one example, the amount in change of this ratio may be mapped to adjustments used by control circuit 88 to adjust the way tank circuit 165 is driven. In another example, the amount of change of this ratio may be mapped to a value for Heat_CO, and this value may then be used to select control parameters to be used in driving tank circuit 165.

The example process described in FIG. 6 may be performed at predetermined time intervals throughout transfer of energy to IMD 2 or as trigger events (e.g., change in recharge current) warrant. In one example, steps in this process may be performed as part of the overall recharge process described in FIG. 4A, with the determination of the change in the peak-to-baseline ratio being used in step 288 of FIG. 4A as an indication of heating of object 8.

A variation of the process of FIG. 6 may be considered by returning to the waveform diagram of FIG. 5. As previously described, waveform 314 represents total power delivered in the absence of object 8 (Power_Charge+Heat_IMD). At a given frequency, the value for Power_Charge can be determined using voltage and current measurements associated with power source 50. From this information, a reference ratio between Power_Charge and the total power delivered to the IMD (i.e., Power_Charge+Heat_IMD) may be derived for any frequency. One or more of these ratios can be saved for later use as reference ratios. For instance, the ratio Power_Charge/(Power_Charge+Heat_IMD) associated with resonant frequency 312 may be saved for this purpose.

Similarly, waveform 310 indicates the total power provided to IMD 2 and object 8. At any given frequency, a ratio may be derived between a corresponding value of Power_Charge and the value obtained from waveform 310, Power_Charge+Heat_IMD+Heat_CO. Because of additional heating attributable to object 8 (i.e., Heat_CO is not equal to zero), the newly-determined ratio will be smaller than the reference ratio. At some predetermined frequency such as system resonant frequency, the amount by which the ratio is smaller than the reference ratio may be used to control power delivery. This may be accomplished in much the same way the peak-to-baseline ratio was used to control power delivery in the method of FIG. 6. This is illustrated in FIG. 7.

Figure 7:
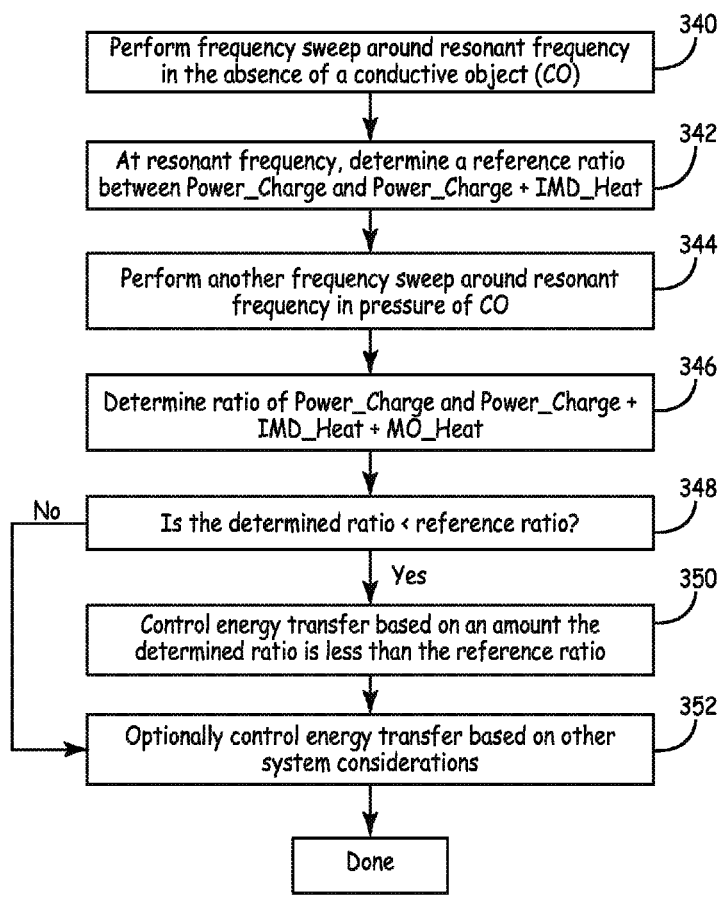
FIG. 7 is an example method of controlling the transcutaneous transfer of energy based on a ratio between power delivered to a rechargeable power source of an IMD and total power delivered transcutaneously to an IMD and object 8 in proximity to the IMD.

FIG. 7 is an example method of using a ratio between Power_Charge and Power_Charge+Heat_IMD+Heat_CO in controlling power delivery in the presence of object 8. Control circuit 88 may drive tank circuit 165 by sweeping the frequencies through the system resonant frequency to derive a power waveform similar to waveform 310 of FIG. 5 (340). At the resonant frequency, a ratio may be determined between Power_Charge and Power_Charge+Heat_IMD (342) This ratio may be saved as a reference ratio for future use in determining heating to be attributed to object 8.

At a later time when object 8 is known to be, or may be, present, another frequency sweep around resonant frequency may be performed, driving primary coil 76 to obtain substantially a same level for Power_Charge to power source 50 at a given frequency as was obtained during the prior sweep (344). At a predetermined frequency such as resonant frequency, a ratio between Power_Charge and Power_Charge+Heat_IMD+Heat_CO may be derived (346).

It may be determined whether this ratio is less than the reference ratio (348). If not, control over power delivery may continue without presently taking into account the heating of object 8, but instead optionally taking into account other system considerations (352). For instance, power delivery may occur based on whether heating associated with primary coil 76 or IMD 2 is a limiting factor in the power delivery, or whether any measured temperatures or currents have exceeded predetermined limits.

Returning to step 348, if the newly-determined ratio is less than the reference ratio, recharge may be controlled based on an amount the newly-determined ratio is less than the reference ratio (350). In one example, the amount in change of this ratio may be mapped to adjustments used by control circuit 88 to adjust the way tank circuit 165 is driven. In another example, the amount of change of this ratio may be mapped to a value for Heat_CO, and this value may, in turn, be used to select control parameters to be used in driving tank circuit 165. Optionally, in addition to exercising control based on the heating of object 8, control of recharge may also be based on some other system considerations (352) such as temperature threshold and/or current threshold limits.

The example process described in FIG. 7 may be performed at various intervals throughout recharge. For instance, steps in this process may be performed as part of the overall recharge process described in FIG. 4A, with the determination of the change in the ratio being used in step 288 of FIG. 4A as an indication of heating of object 8, for example.

Still other variations of the above-described processes are possible. For instance, according to one method, a frequency sweep may be performed to locate the resonant frequency of charging system 48 and IMD 2 in the absence of object 8. At the resonant frequency, the power delivered to the primary coil, Power_Primary, may be determined. Also at this frequency, the RMS current in the primary coil may be determined. The AC series resistance of the primary coil 76 at resonant frequency may be determined by dividing Power_Primary by the square of the RMS current. This reference value may be saved for future reference.

At a later time, when object 8 is present, the above-described process may be repeated to determine the resonant frequency of the system when object 8 is in proximity to IMD 2. At this frequency, the AC series resistance of coil 76 in the presence of object 8 may be determined. This AC series resistance may be higher in the presence of object 8 because of the loading of object 8 on the system. The amount by which the AC series resistance of the coil increases in the presence of object 8 is proportional to the loading presented by object 8, and further is proportional to Heat_CO. This amount of increase of the AC series resistance may be associated with a threshold and may be used to adjust the manner in which energy is transferred to IMD 2 according to any of the methods described above, including adjusting duty cycle and/or voltage of the H-bridge circuit to change Power_Primary.

Still other types of frequency sweep data may be used to control power delivery. This is described in reference to FIG. 8.

Figure 8:
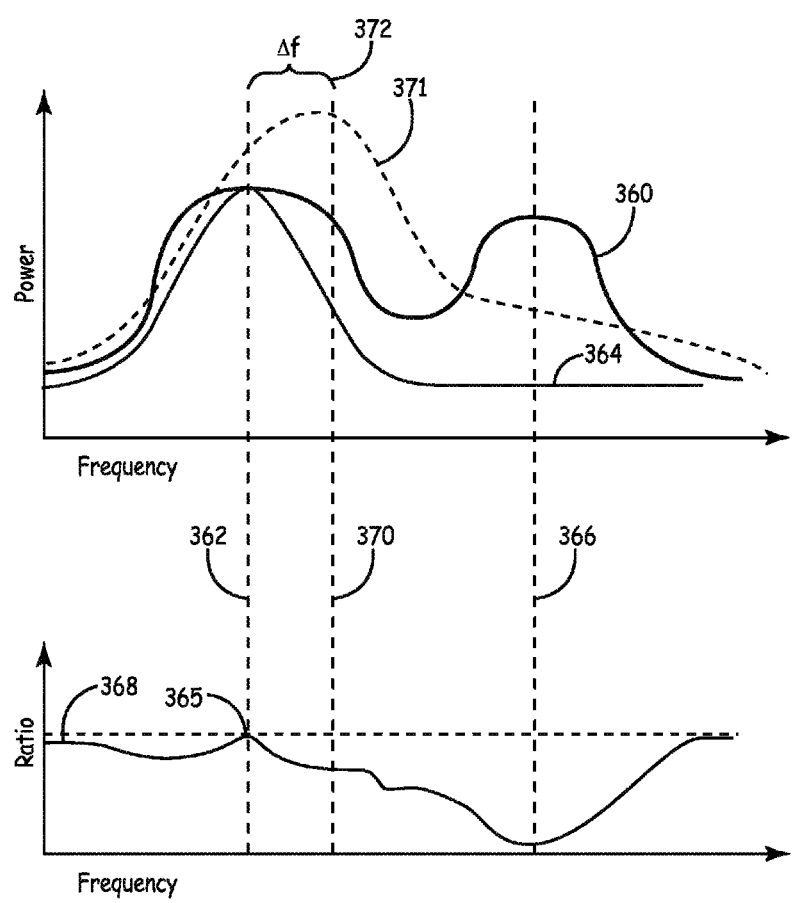
FIG. 8 is an example waveform diagram of loading profiles obtained when transcutaneously transferring energy to an IMD over a range of frequencies.

FIG. 8 is another example waveform diagram illustrating use of a loading profile in controlling the transcutaneous transfer of energy. In this case, the frequency sweep results in an additional peak that occurs around a frequency 366 that is a resonant frequency for object 8. At this frequency, a maximum amount of heating may occur for object 8.

In the example of FIG. 8, waveform 364 is similar to waveform 314, representing the sum of Power_Charge and Heat_IMD. As was described above, this waveform may be obtained by performing a frequency sweep while IMD s is contained in a controlled environment that models a body environment and in the absence of object 8. For instance, the waveform may be obtained while IMD is positioned within a gel bath. Alternatively, the waveform may be obtained post-implant before object 8 is present. In one example, processing steps that are similar to those described above may be used to derive this waveform as Power_Primary−Heat_Primary. Waveform 364 may be stored for later use after IMD 2 has been implanted in a patient in a manner that is substantially similar to the scenario modeled to obtain the loading profile.

Another waveform 360 may be obtained while IMD 2 is known or suspected to be positioned within the presence of object 8 (e.g., after implant in a person that carries such an object.) This waveform may be determined using methods such as those described above with respect to derivation of waveform 310.

Also shown in FIG. 8 is an example waveform 368 illustrating a ratio between values of waveform 364 and those of waveform 360. At the system resonant frequency 362 for IMD 2 and charging circuit 70, the ratio between the value contained in waveform 364 and the value of waveform 360 approaches "one" in the current example as indicated by point 365 of waveform 368. This represents the frequency at which the most energy is being transferred to power source 50. This ratio drops to a lower value at frequency 366, which is a resonant frequency associated with object 8. The drop in the ratio at frequency 366 indicates that at this frequency, more heat is being dissipated by object 8 and less energy is being transferred to power source 50. This decrease in the value of the ratio may be used to control energy transfer as discussed further below.

As represented by waveforms 360 and 364, a frequency sweep in the presence of object 8 may yield a loading profile that reveals a resonant frequency associated with object 8. This resonant frequency may be relatively distant from the resonant frequency associated with IMD 2, as indicated by the scenario of waveform 360. The way in which this information may be used to control recharge is discussed further below.

Next, consider a different implant scenario than that associated with waveform 360. In this different scenario, a different object 8 (with different physical characteristics) and/or a different placement relative to IMD 2 may be in proximity to the IMD during the frequency sweep, for instance. Because of the differences associated with this scenario as compared to the previous scenario that yielded waveform 360, a very different loading profile is obtained as compared to that shown by waveform 360. This new loading profile is represented by waveform 371 (shown dashed). In this case, the peak for waveform 371 is relatively close to, and subsumes, the peak for waveform 364. This indicates that an overall resonant frequency of the system has shifted to a higher frequency 370 as compared to the resonant frequency of a system that includes only IMD 2 and charging circuit 70, as indicated by waveform 364 and the corresponding peak at frequency 362.

When the loading profile of the system is changed (e.g., either by the presence of a new peak at frequency 366 as indicated by waveform 360 associated with a first implant scenario or a shift in the overall resonant frequency as indicated by dashed waveform 371 associated with a different implant scenario) the change in the loading profile may be used to control power delivery in a number of different ways.

If the loading profile indicates object 8 is causing a shift in the overall resonance frequency of the system as indicated by dashed waveform 371, the amount by which the frequency shift occurred may be used as an indication of the likely amount of heating due the presence of object 8. For instance, in FIG. 8, the resonant frequency of the system shifted by an amount Δf 372. In one example, the size of the frequency shift may be mapped to a Heat_CO value. A mapping function that maps Δf 372 to Heat_CO can be determined empirically by changing proximity of the object 8 to IMD 2 to affect the loading profile in various ways and determining the resulting heating associated with object 8 for each of the configurations. A function may then be derived that relates the size of the change in resonant frequency of the loading profile to Heat_CO. Alternatively, such a function between the size of the frequency shift and Heat_CO may be determined via modeling using known modeling techniques.

Once a value for Heat_CO is determined based on the size of the frequency shift, 372, the Heat_CO value may be compared to a threshold to determine what type of adjustments need to be made by control circuit 88 in driving tank circuit 165. Such adjustments may involve adjustments to duty cycle and/or voltage, as discussed in reference to FIGS. 4A and 4B, for example. As further described in reference to these figures, in some examples, an amount by which Heat_CO exceeds a threshold may be mapped to changes in the way control circuit 88 will drive tank circuit 165 (e.g., changes in duty cycle or voltage). Such mapping may occur, for instance, via lookup tables so that control circuit 88 may readily determine how to adjust driving tank circuit in a given circumstance. In another embodiment, the changes in the way the tank circuit will be driven can be obtained by a mapping the size of the frequency shift 372 directly to these changes. This eliminates the intermediate step of first deriving a value for Heat_CO, which is then used to obtain the drive parameters for tank circuit 165.

Waveform 371 may be used in other ways to control the transfer for energy. For instance, it may be observed that at frequencies below frequency 362, waveform 371 has not yet diverged substantially from waveform 364. Thus, it may be desirable to perform recharge slightly below frequency 362 because at these slightly lower frequencies, heating associated with the object 8 is minimal, and may even be able to be ignored for practical purposes when transferring energy to IMD 2. In contrast, at frequencies of 362 or higher, heating associated with object 8 is more substantial, as indicated by the divergence between waveform 364 and waveform 371. While a slightly lower frequency may not coincide exactly with the resonant frequency of IMD 2, it may never-the-less be "good enough" to transfer adequate energy to IMD 2 while also maintaining heating of object 8 at desired levels. Thus, in one example, the loading profile may be used to determine a slightly different frequency range for use in transferring energy to IMD to control heating.

Yet another example use of the loading profile of FIG. 8 may be considered based on waveforms 360, 364 and 368. From these waveforms, it may be determined that the resonant frequency 362 associated with IMD 2 has not change substantially because of the presence of object 8. It may further be determined that the ratio represented by waveform 368 between Power_Charge+Heat_IMD and Power_Charge+Heat_IMD+Heat_CO remains close enough to one so that energy transfer need not change at the resonant frequency 362. In this case, energy may be transferred to IMD at resonant frequency 362 as though object 8 were not present, assuming frequency tuning can maintain the frequency sufficiently close to frequency 362. At this resonant frequency, heat dissipation for object 8 is not substantial. Only at frequencies relatively removed from frequency 362, such as around frequency 366, does heating of object 8 become more substantial. Thus, the additional steps of determining heating for object 8 may be eliminated so long as the transfer of energy occurs at frequency 362, with the primary considerations associated with this transfer of energy being heating associated with primary coil 76 and IMD 2.

Therefore, it may be appreciated that loading profiles may be used in a variety of ways to control the transfer of energy from system 48 to IMD 2.

Figure 9:
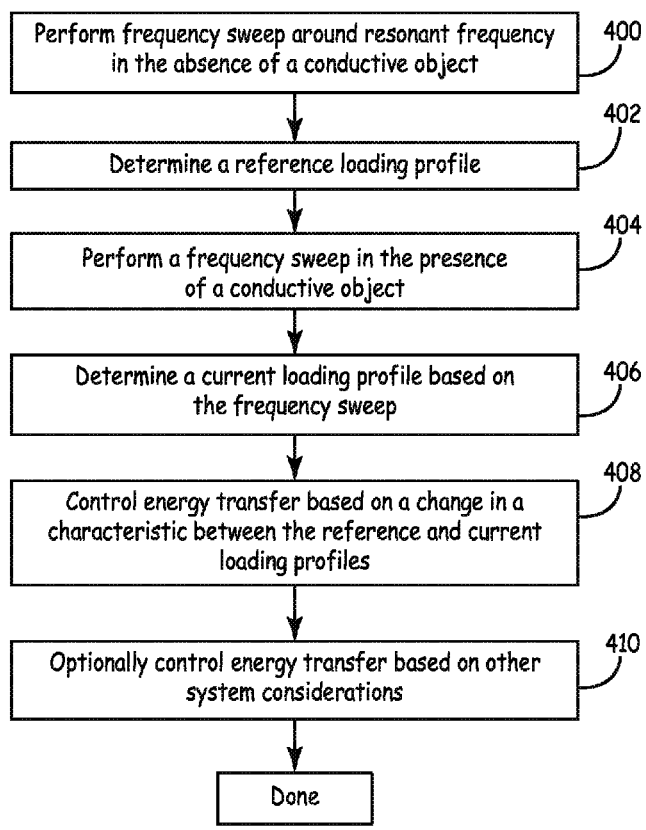
FIG. 9 is a flow diagram illustrating one example method of controlling transcutaneous transfer of energy based on loading profiles.

FIG. 9 is a flow diagram illustrating one example method according to the foregoing discussion. A frequency sweep may be performed by control circuit 88. This frequency sweep may be performed around the resonant frequency of the system that includes system 48 and IMD 2 in the absence of object 8 (400). From this frequency sweep, a reference loading profile may be determined (402). This profile may include a waveform of Power_Primary−Heat_Primary in the absence of object 8, for instance.

Later, at a time when object 8 is known or suspected to be present, another frequency sweep may be performed around the resonant frequency (404). This sweep may be used to determine a current loading profile (406). Recharge may be controlled based on a change in a characteristic between the reference and current loading profile (408). Such a change may be a size of a shift of the system resonant frequency, or a determination that the current loading profile indicates a frequency range that may be employed to transfer energy to IMD 2 (e.g., a range around the resonant frequency or slightly above or below resonant frequency in some cases.) If desired, recharge control may also be based on other considerations (410), such as temperature measurements taken in regards to IMD 2, primary coil 76 and/or system 48.

Thus, some of the techniques described herein utilize loading profiles to control power delivery to IMD 2 that is in proximity to object 8. Still other methods for controlling power delivery during recharge may depend on a positional map that relates a relative position between primary coil 76 and IMD 2 to power transfer values. According to this embodiment, a positional map is developed based on a recharge session performed when IMD is implanted, or otherwise placed in a controlled environment, in the absence of object 8. The positional map associates positional data (data describing a relative position between IMD 2 and primary coil 76) with respective power information similar to that discussed above (e.g., Power_Charge occurring at a given relative position between IMD and primary coil).

To obtain a positional map, control circuit 88 may drive tank circuit 165 to maintain Power_Primary−Heat_Primary at a relatively constant level while antenna 78 is moved to different relative positions with respect to IMD 2. For each position, a value for Power_Charge may be recorded using above-described techniques. Optionally, if it is known that the voltage to power source 50 remains substantially constant prior to entering "top off" of power source 50, only the current being provided to power source 50 need be recorded rather than determining both current and voltage levels so that Power_Charge may be derived.

Additionally, positional data may be recorded at each position for which the power data is collected. This positional data indicates the relative position between antenna 78 and IMD 2. To obtain this positional data, antenna 78 may be maintained in a predetermined relative orientation with respect to the patient, such as having a particular point on antenna 78 pointing "up" (e.g., in reference to the S-I axis of the patient) while the patient is in an upright position, for instance. Optionally, a second point on antenna 78 may be pointing in another predetermined direction relative to the patient (e.g., "right" along an L-M axis of the patient's body). While antenna 78 is maintained in this orientation relative to the patient's body, the antenna 78 may be systematically moved to various positions relative to IMD 2. This re-positioning may follow a grid-like pattern. At each point on this grid, positional data may be collected that describes the relative positioning of primary coil 76 with respect to secondary coil 56.

For instance, signal strength indicator (SSI) values may be collected in association with each of multiple triangulating antennas carried at various locations on, or within, antenna 78. Such triangulating antennas may be activated one-by-one. Each activated antenna may transmit a telemetry signal between antenna 78 and IMD 2. During the transmission of a signal in this manner, an SSI value may be collected for the individual triangulating antenna. This SSI values may reflect a signal strength obtained in associated with the telemetry transmission to and/or from IMD 2 and this triangulating antenna. The relative signal strength associated with each triangulating antenna will provide a relative position of each of the triangulation antennas with respect to IMD 2, and hence will provide a relative positioning of antenna 78 in regards to IMD 2. Such relative positioning will indicate whether, and by how much, antenna 78 is "above" or "below" IMD 2 with respect to an S-I axis of the patient's body. Similarly, this relative positioning data will indicate whether, and by how much, antenna 78 is positioned laterally or medially with respect to an L-M axis of the patient's body. The use of SSI values in positioning an antenna 78 relative to IMD 2 is described in commonly-assigned U.S. patent Ser. No. 12/100,875 filed on Apr. 10, 2008 entitled "Using Telemetry Coupling as a Surrogate for Recharge Coupling", which is incorporated herein by reference to the extent such application is not inconsistent with the current disclosure.

The positioning data (e.g., the collection of SSI values for each of the triangulating antennas obtained for a given position of antenna 78) may be stored along with power data obtained at the given position. The power data may be obtained by activating primary coil 76 and determining a value for Power_Charge obtained while Power_Primary−Heat_Primary is maintained at a relatively constant level.

As another example of recording positioning data, triangulating recharge coils may be carried by antenna 78 in addition to primary coil 76. These triangulating recharge coils may be located at various positions on, or in, antenna 78. These coils may be sequentially enabled to transmit a predetermined burst of power to IMD 2 while recharge current to power source 50 is measured. The recharge current level measured for each such triangulating coil will provide an indication as to the distance of each coil from secondary coil 56 of IMD 2. Assuming antenna 78 is maintained in a same orientation relative to the S-I and L-M axis of the patient's body as the antenna 78 is moved to each position, this data may be used to determine the relative position of antenna 78 with respect to IMD 2 in reference to the S-I and L-M axis of the patient's body. For instance, such data will provide an indication of whether, and by how much, antenna 78 is above or below IMD 2 with respect to the S-I axis of the patient's body. Such data may further provide an indication of whether, and by how much, antenna 78 is to the right or left of IMD 2 with respect to the L-M axis of the patient's body. As was the case with the SSI values, this information may be stored with power data obtained by activating primary coil 76 at a given position. An example technique for deriving positional data according to a similar method is provided in U.S. Pat. No. 7,806,122 entitled "Septum Port Locator System and Method for an Implantable Substance Delivery Device", which is incorporated by reference to the full extent such patent is not inconsistent with the current disclosure.

This relative positioning data may be augmented by one or more accelerometers carried by antenna 78 and IMD 2. Assuming the accelerometer orientations within IMD 2 and antenna 78 are known, the orientation of IMD 2 within the patient is known, and the orientation of antenna 78 is maintained in a predetermined manner with respect to body axis of the patient while moving from position to position, the relative angles between the primary and secondary coils may be calculated and stored within the positional map to help identify a particular relative relationship between the primary and secondary coils.

In the foregoing manner, the positional data may take into account such things as distance between IMD and antenna 78, relative angles of primary coil 76 relative to secondary coil 56, and an offset between the two devices (e.g., offset between IMD 2 and antenna 78 along one or more the S-I or L-M axes of the patient, etc.) This type of data may be collected once after IMD is implanted in the absence of object 8. This collection of data may be embodied as a lookup table storing the associations between a given relative IMD/antenna position and the power or current data. This data may be stored as a positional map within a storage device of IMD, system 48 and/or external device 100 for later use.

Next, the transfer of power to IMD 2 may be initiated when object 8 is positioned in proximity to IMD 2 such that heating of object 8 may occur. During the transfer of energy to IMD 2, tank circuit 165 may be driven to obtain substantially a same level for Power_Primary−Heat_Primary as was used when the positional map was generated. As the antenna 78 is moved from position-to-position in the vicinity of IMD 2, positional information may be obtained to describe the relative position between antenna 78 and IMD 2. This data may be obtained from the triangulation antennas and/or other positional sensors carried by IMD 2 and antenna 78 in the manner previously described. This positional data may be used to reference the previously-recorded positional map to locate the entry within the positional map having positional data that is most similar to that currently recorded. The power data associated with this entry may be retrieved and compared to power data currently being obtained in the presence of object 8. Specifically, if Power_Charge is less than was previously recorded for the same total power delivery of Power_Primary−Heat_Primary by some predetermined amount, it may be concluded that at this position, some power is now being lost to heat dissipation in object 8. The amount by which Power_Charge is currently less than previously recorded in the positional map may be used to control power delivery using techniques similar to those described with respect to the above-described techniques. For instance, the amount by which Power_Charge is less than expected may be used to vary a duty cycle and/or voltage level of the driving circuit when the antenna is maintained in the corresponding position.

In one embodiment, feedback may be provided to guide the user in placing antenna 78 into a location wherein the difference between the current level for Power_Charge and the level recorded within the positional map when object 8 was absent is less than some predetermined threshold value. This position may also be required to be a location for primary coil 76 wherein at least some predetermined minimum power level is achieved for Power_Charge. In this manner, the user may be aided in positioning antenna 78 such that the amount of power being lost to heat dissipation in object 8 is minimized while an adequate level of power is being delivered to IMD 2 for use in charging power source 50.

In some examples, while antenna 78 is moved about in proximity to IMD, one or more locations that are considered acceptable for recharge may be determined and saved. At this location, adequate recharge current is obtained (as may be determined by measuring recharge current) while Heat_CO is maintained below acceptable thresholds (as may be determined in a manner previously described.) These positions may be recorded, as by recording the triangulation values determined by the triangulating antennas. Thereafter, this recorded positional information may be used by the system to aid the user in re-positioning antenna 78 in one of these acceptable locations during future recharge sessions. For instance, visual or audio feedback may be provided via a user interface to aid the user in so positioning antenna 78.

As may be appreciated, this technique involves performing processing intensive measurements to determine relative position between antenna 78 and IMD 2 throughout the recharge process as antenna 78 is moved, and for this reason, may not be desirable in some types of systems.

As yet another variation of the foregoing positional map, an array of primary coils may be substituted for single primary coil 76. The array of primary coils may be located at a predetermined position relative to IMD 2 during a characterization process that develops data for a positional map when IMD is not located in the presence of object 8. To generate the positional map, each coil of an array can be selectively individually activated at a predetermined power level so that the values for Power_Charge and Heat_IMD are recorded in association with this coil and the data stored for later use. Later, when IMD is, or may be, in the presence of object 8 and the array is positioned in a manner substantially similar to the way in which it was placed when the map was generated, the coils may again be systematically individually driven. The coils may be driven using substantially similar drive parameters as when the map was generated (e.g., such that Power_Primary−Heat_Primary is substantially the same as before). If a value of Power_Charge is below that previously recorded in the absence of object 8, it may be concluded that more heat is now being dissipated by object 8. A coil may be selected for use that results in the difference between the present level for Power_Charge and the level recorded within the positional map being less than some predetermined value. This position may also be one wherein at least some minimum power level is achieved for Power_Charge. As in cases described above, in any of these processes, a value for the recharge current may serve as a surrogate for Power_Charge assuming that voltage of power source 50 remains substantially constant throughout recharge until top-off occurs.

Figure 10:
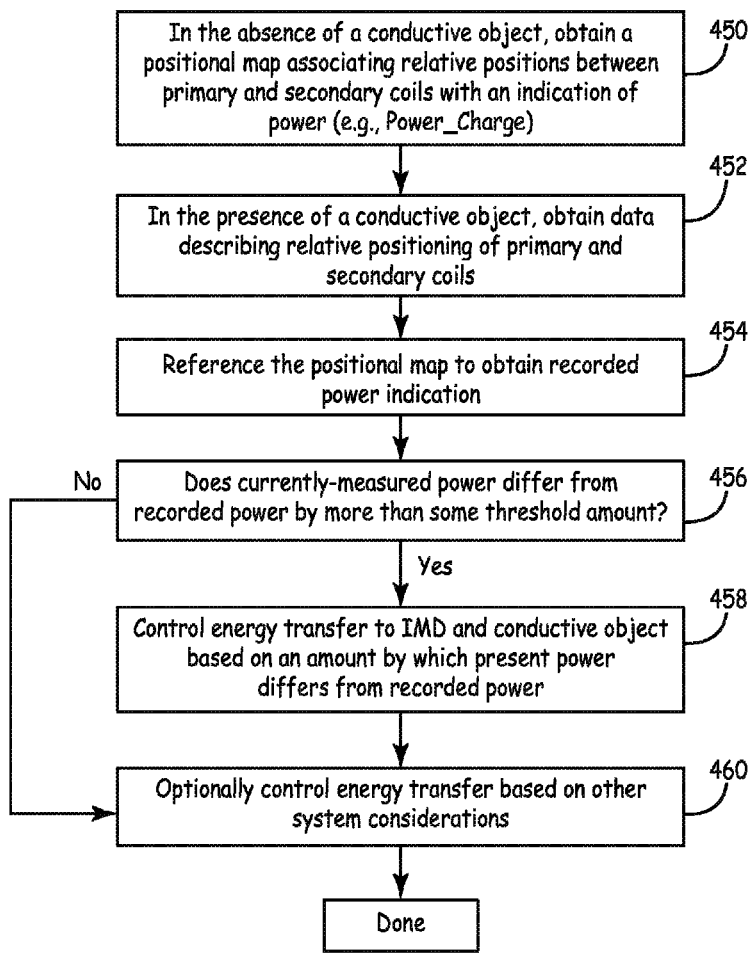
FIG. 10 is one example method of using a positional map to control recharge.

FIG. 10 is one example method of using a positional map to control recharge. First a positional map may be recorded in the known absence of object 8 while the power being supplied to IMD is substantially maintained at a constant level (e.g., Power_Primary−Heat_Primary is maintained at a constant level) (450). Such a map may be recorded for a given implant scenario, may be a map provided by a manufacturer in association with a given charging circuit 70 and IMD 2, or may be recorded prior to implant of IMD 2 while this device is in a controlled environment that emulates an implant scenario. This map contains associations between relative positions of the primary and secondary coils and values for determined power levels, such as values for Power_Charge and Heat_IMD.

After the positional map has been populated with data, this map may be used to control energy transfer when IMD 2 is in the presence of object 8 as follows. Energy transfer may be initiated using substantially a same frequency, substantially a same relative orientation of antenna 78 to the patient's body, substantially a same implant scenario (e.g., implant depth and angle of secondary coil) and substantially a same power delivery level as was used to create the positional map. Antenna 78 may then be moved in the vicinity of IMD 2 using a grid-like pattern that may be substantially similar to that used during creation of the positional map.

At each position to which antenna 78 is moved, data describing a relative position between primary and secondary coils may be obtained using methods described above (452). This data describing the relative position between the primary and secondary coils may be used to reference the positional map to locate an entry within the positional map having positional data that is substantially similar to the currently-obtained positional data. From this entry, the recorded power indication (e.g., Power_Charge) for this relative position between primary and secondary coils may be obtained (454). It may then be determined whether a value for Power_Charge for this position as currently measured in the presence of object 8 differs from the previously-recorded value for Power_Charge by more than some threshold amount (456). For instance, Power_Charge may be less than the recorded value because some power that had previously been used to generate the recharge current is now being absorbed by object 8. If Power_Charge differs from than the previously-recorded value by more than the threshold amount, it may be determined heating for object 8 exceeds acceptable levels.

If it is determined that Power_Charge differs from the previously recorded value by more than the threshold amount, control over energy transfer to IMD and object 8 may be performed based on an amount by which the present power value differs from the recorded value, using any of the methods described here (458). Optionally, control over energy transfer to IMD and object 8 may also be based on other considerations, such as temperature thresholds or current thresholds (460). If, in step 456, the determination that the current power level is not less than the recorded power level by more than the threshold amount, control over energy transfer to IMD and object 8 may be based solely on these other consideration (460), or energy transfer may simply remain unchanged.

Some of the steps of the method of FIG. 10 may be performed once at the start of a recharge session. For instance, steps 452-460 may be performed while a patient is locating antenna 78 with respect to IMD 2 at the start of recharge. Alternatively, these steps may be repeated at predetermined time intervals during a recharge session so that energy delivery is controlled throughout the recharge session. This may be desirable to compensate for movement of antenna 78 as the patient moves or changes posture. In another embodiment, steps 452-460 may be repeated during a recharge session based on an occurrence of a trigger event, such as a change in recharge current or Power_Charge, or an indication from a sensor such as an accelerometer that antenna 78 moved.

The current disclosure primarily discusses the presence of a single object 8. It will understand that this is for simplicity only and is not intended to be limiting. The techniques described herein may be applied in the presence of any number of objects that conduct current within the presence of an electromagnetic field, with the value for Heat_CO representing the cumulative heating of all objects that are present during the transfer of transcutaneous energy. Modeling or empirical techniques can be used to determine which object of a plurality of such objects will be associated with heating that represent the limiting factor for a given set of energy transfer conditions (e.g., frequency, antenna location, duty cycle, etc.) Based on this determination, a threshold for Heat_CO can be determined accordingly. Thus, any number of objects may be present during recharge, with techniques described herein being used to control power delivery such that heating is limited is a desired manner. In some cases, the one or more objects may be one or more other IMDs.

As previously discussed, conductive objects may be carried on and/or within a patient's body. In some cases, these objects may be other IMDs, such as other stimulation or drug delivery devices. In some cases, these objects may be capable of communicating with charging system 48 and/or external device 10. Further, one or more of the objects may perform methods similar to those discussed in reference to IMD 2 to measure currents and/or voltages that may be used in determining how energy transfer may be controlled. Thus, multiple implanted and/or external devices may perform functions similar to those ascribed to IMD 2 to control energy transfer according to the current disclosure. Moreover, multiple external devices may perform functions ascribed to charging system 48 and/or external device in accordance with the disclosure to control energy transfer.

While the foregoing discussion provides some examples of supplying power to rechargeable power source 50 so that IMD 2 can operate from the power stored by this power source, other embodiments of the disclosure provide transcutaneous power to IMD 2 so that IMD may operate directly from the transferred energy without storing the power in power source 50 before it is used. In these embodiments, it may be desirable to monitor the voltage and current flowing to the IMD circuits in a manner similar to the way in which the charging current and voltage are measured in the above-described embodiments. In such embodiments, all power delivered to IMD 2 may be directed to Heat_IMD in the absence of object 8, while power delivered to IMD 2 will be directed to both Heat_IMD and Heat_CO in the presence of object 8. Control of energy transfer may be based on Heat_CO and Heat_IMD using techniques described above.

It will be appreciated that many embodiments are contemplated by the current disclosure. The specific embodiments described are to be considered exemplary only and not limiting and the present disclosure is limited only by the claims that follow.

What is claimed is:

1. A system to transfer energy to an Implantable Medical Device (IMD) that is located in proximity to a conductive object that is associated with an estimated amount of heat, comprising:
a primary coil configured to transcutaneously transfer energy to the IMD located in proximity to the conductive object; and
processing circuitry configured to control the transfer of energy to the IMD based on the estimated amount of heat associated with the object during the transfer of energy to the IMD, wherein the IMD comprises a housing and the conductive object is located outside of the housing.

2. The system of claim 1, wherein the processing circuitry is configured to determine the amount of heat dissipated by the object and to control the transfer of energy based on the determined amount.

3. The system of claim 1, wherein the processing circuitry is configured to vary a frequency at which the primary coil is driven to determine respective loading profiles of the system in the presence of the object and in the absence of the object and to control the transfer of energy based on the respective loading profiles.

4. The system of claim 3, wherein the processing circuitry is configured to control the transfer of energy based on a peak-to-baseline ratio indicated by at least one of the respective loading profiles.

5. The system of claim 1, wherein the processing circuitry is configured to control the transfer of energy based on at least one predetermined characteristic of the object.

6. The system of claim 1, wherein the processing circuitry is configured to control the transfer of energy based on heating of the IMD.

7. The system of claim 1, wherein the processing circuitry is configured to control the transfer of energy based on a change in a ratio between power delivered to a power source of the IMD and total heat dissipation within the system.

8. The system of claim 1, wherein the processing circuitry is configured to control the transfer of energy based on a positional map containing associations, each association associating a relative position between the primary coil and a secondary coil of the IMD and an indication of a power level obtained when energy is transferred from the primary coil to the secondary coil when the primary coil is in the relative position with respect to the secondary coil.

9. The system of claim 8, wherein one or more relative positions between the primary coil and the secondary coil are selected based on the positional map for use in transferring energy from the primary coil to the secondary coil, and wherein feedback is provided to a user to guide the user in locating the primary coil in one of the relative positions with respect to the secondary coil.

10. The system of claim 1, further comprising the Implantable Medical Device (IMD), and wherein the IMD is configured to perform at least one of providing a therapy and sensing a signal.

11. The system of claim 1, wherein the conductive object comprises a second implantable medical device located in proximity to the IMD.

12. The system of claim 1, wherein the IMD is configured to be implantable within a patient's body, and wherein the conductive object comprises at least one conductive object configured to be carried on the exterior of the patient's body.

13. The system of claim 1, wherein the IMD is configured to be implantable within a patient's body, and wherein the conductive object comprises a collection of multiple objects configured to be positioned at one or more locations of the patient's body.

14. The system of claim 1, wherein the object is separated by some distance from the IMD while being close enough to the IMD to receive some of the energy transcutaneously transferred to the IMD.

15. A method, comprising:
transcutanously transferring energy to an implantable medical device (IMD) that is located in proximity to a conductive object; and
controlling, via processing circuitry the transcutaneous transfer of energy to the IMD based on an estimated amount of heat associated with the object during the transfer of the energy, wherein the IMD comprises a housing and the object is located outside of the housing.

16. The method of claim 15, further comprising determining the amount of heat dissipated by the object and wherein controlling the transfer of energy comprises controlling the transfer of energy based on the determined amount of heat dissipated by the object.

17. The method of claim 15, further comprising varying a frequency at which the transfer of energy occurs to determine a loading profile and wherein controlling the transfer of energy comprises controlling the transfer of energy based on the loading profile.

18. The method of claim 17, further comprising determining a difference between a resonant frequency of the determined loading profile and a resonant frequency of a reference loading profile, and where controlling the transfer of energy comprises controlling the transfer of energy based on the difference.

19. The method of claim 15, further comprising determining a peak-to-baseline ratio for power delivery at a resonant frequency, and wherein controlling the transfer of energy comprises controlling the transfer of energy based on the peak-to-baseline ratio.

20. The method of claim 15, further comprising controlling the transfer of energy based on at least one predetermined characteristic of the object.

21. The method of claim 15, further comprising controlling the transfer of energy based on at least one of heat dissipated by the primary coil and heat dissipated by the IMD.

22. A system to transfer energy to an implantable medical device (IMD) that is located in proximity to another object, the other object being conductive and being associated with an estimated amount of heat, comprising:
means for transcutanously transferring energy to the IMD located in proximity to the conductive object; and
means for controlling the transfer of energy to the IMD based on the estimated amount of heat associated with the object during the transfer of energy, wherein the IMD comprises a housing and the object is located outside of the housing.

23. A non-transitory storage medium for storing instructions to cause a control circuit to:
transcutanously transfer energy to an implantable medical device (IMD) that is located in proximity to a conductive object; and
control the transfer of energy to the IMD based on an estimated amount of heat associated with the object during the transfer of energy, wherein the IMD comprises a housing and the object is located outside of the housing.

24. The storage medium of claim 23, wherein the instructions further cause the control circuit to varying a frequency at which the transfer of energy occurs to determine a loading profile and to control the transfer of energy based on a characteristic of the loading profile.

25. The storage medium of claim 24, wherein the instructions further cause the control circuit to determine respective loading profiles in the presence and absence of the conductive object and to control the transfer of energy based on a difference between the respective loading profiles.

26. The storage medium of claim 23, wherein the instructions further cause the control circuit to control the transcutaneous transfer of energy based on a determined amount of heat dissipated by the object.

27. The storage medium of claim 26, wherein the instructions further cause the control circuit to determine the amount of heat dissipated by the object based on an amount of power provided to a rechargeable power source of the IMD and an amount of heat dissipated by the IMD.

28. The storage medium of claim 23, wherein the instructions further cause the control circuit to estimate the amount of heat associated with the object based on a difference between an amount of power delivered by a primary coil in the presence of the conductive object to achieve a predetermined level of power delivered to a rechargeable power source of the IMD as compared to an amount of power delivered by the primary coil in the absence of the conductive object to achieve the predetermined level of power delivered to the rechargeable power source.

* * * * *